(12) United States Patent
Ebbers et al.

(10) Patent No.: US 12,133,674 B2
(45) Date of Patent: Nov. 5, 2024

(54) TATTOO REMOVAL

(71) Applicant: Pulse Biosciences, Inc., Hayward, CA (US)

(72) Inventors: Edward A. Ebbers, San Carlos, CA (US); Darrin R. Uecker, San Mateo, CA (US); Richard L. Nuccitelli, Millbrae, CA (US)

(73) Assignee: Pulse Biosciences, Inc., Hayward, CA (US)

( * ) Notice: Subject to any disclaimer, the term of this patent is extended or adjusted under 35 U.S.C. 154(b) by 482 days.

(21) Appl. No.: 17/041,420

(22) PCT Filed: Mar. 20, 2020

(86) PCT No.: PCT/US2020/023882
§ 371 (c)(1),
(2) Date: Sep. 24, 2020

(87) PCT Pub. No.: WO2020/191301
PCT Pub. Date: Sep. 24, 2020

(65) Prior Publication Data
US 2021/0401489 A1 Dec. 30, 2021

Related U.S. Application Data

(60) Provisional application No. 62/821,959, filed on Mar. 21, 2019, provisional application No. 62/884,643, filed on Aug. 8, 2019.

(51) Int. Cl.
*A61B 18/14* (2006.01)
*A61B 18/18* (2006.01)
(Continued)

(52) U.S. Cl.
CPC ........ *A61B 18/1477* (2013.01); *A61B 18/203* (2013.01); *A61B 34/10* (2016.02);
(Continued)

(58) Field of Classification Search
CPC .............. A61B 18/1477; A61B 18/203; A61B 2017/00464; A61B 2017/00769;
(Continued)

(56) References Cited

U.S. PATENT DOCUMENTS 5,683,366 A * 11/1997 Eggers ............... A61B 18/1482
604/114
6,326,177 B1 12/2001 Schoenbach et al.
(Continued)

OTHER PUBLICATIONS

Hinman et al.; U.S. Appl. No. 16/980,347 entitled "Moving electrodes for the application of electrical therapy within a tissue," filed Sep. 11, 2020.

*Primary Examiner* — Michael F Peffley
*Assistant Examiner* — Amanda L Zink
(74) *Attorney, Agent, or Firm* — Shay Glenn LLP

(57) ABSTRACT

Described herein are methods and apparatuses for the application of electric energy treatment(s) to skin tissue to alter pigmentation, and in particular to remove a tattoo. These methods and apparatuses may deliver pulsed electrical energy having a pulse duration in submicrosecond pulse range to provide high-field strength pulses that may effectively release tattoo ink and allow removal of tattoo ink regardless of ink color or composition.

25 Claims, 24 Drawing Sheets

(51) Int. Cl.
  *A61B 18/20* (2006.01)
  *A61B 34/10* (2016.01)
  *A61B 34/20* (2016.01)
  *A61B 34/32* (2016.01)
  *A61B 17/00* (2006.01)
  *A61B 18/00* (2006.01)

(52) U.S. Cl.
  CPC .............. *A61B 34/20* (2016.02); *A61B 34/32* (2016.02); *A61B 2017/00769* (2013.01); *A61B 2018/0047* (2013.01); *A61B 2018/00994* (2013.01); *A61B 2018/143* (2013.01); *A61B 2034/2065* (2016.02)

(58) Field of Classification Search
  CPC .. A61B 2018/0047; A61B 2018/00613; A61B 2018/00994; A61B 2018/0293; A61B 2018/143; A61B 2018/1462; A61B 2018/1495; A61B 2034/2053; A61B 2034/2065; A61B 2090/3937; A61B 34/10; A61B 34/20; A61B 34/30; A61B 34/32
  See application file for complete search history.

(56) References Cited

U.S. PATENT DOCUMENTS

| | | | |
|---|---|---|---|
| 7,981,112 B1 | 7/2011 | Neev | |
| 8,000,813 B2 | 8/2011 | Schoenbach et al. | |
| 8,512,334 B2 | 8/2013 | Nuccitelli et al. | |
| 8,822,222 B2 | 9/2014 | Beebe et al. | |
| 9,101,764 B2 | 8/2015 | Nuccitelli et al. | |
| 9,656,055 B2 | 5/2017 | Weissberg et al. | |
| 9,724,155 B2 | 8/2017 | Nuccitelli et al. | |
| 9,956,391 B2 | 5/2018 | Weissberg et al. | |
| 10,154,876 B2 * | 12/2018 | Callas | A61B 18/14 |
| 10,252,050 B2 | 4/2019 | Kreis et al. | |
| 10,850,095 B2 | 12/2020 | Ebbers et al. | |
| 10,857,347 B2 | 12/2020 | Danitz et al. | |
| 11,857,212 B2 * | 1/2024 | Capelli | A61B 17/22004 |
| 2002/0161362 A1 * | 10/2002 | Penny | H05H 1/466 606/41 |
| 2005/0177143 A1 | 8/2005 | Bullington et al. | |
| 2010/0262135 A1 * | 10/2010 | Berube | A61B 18/1477 606/33 |
| 2011/0092973 A1 | 4/2011 | Nuccitelli et al. | |
| 2014/0343416 A1 * | 11/2014 | Panescu | A61B 34/30 600/431 |
| 2014/0364797 A1 | 12/2014 | Schoenbach et al. | |
| 2015/0201991 A1 | 7/2015 | Zemlin | |
| 2016/0192961 A1 * | 7/2016 | Ginggen | A61B 17/14 604/173 |
| 2016/0331439 A1 * | 11/2016 | Winkelman | A61B 18/1477 |
| 2017/0245928 A1 | 8/2017 | Xiao et al. | |
| 2017/0246440 A1 * | 8/2017 | Kalghatgi | H05H 1/2406 |
| 2017/0246455 A1 | 8/2017 | Athos et al. | |
| 2017/0319851 A1 | 11/2017 | Athos et al. | |
| 2018/0078755 A1 | 3/2018 | Kreis et al. | |
| 2018/0243558 A1 | 8/2018 | Athos et al. | |
| 2019/0046791 A1 * | 2/2019 | Ebbers | A61N 1/0476 |
| 2019/0217080 A1 * | 7/2019 | Moss | A61N 1/0502 |
| 2020/0197077 A1 | 6/2020 | Winkelman et al. | |
| 2020/0197078 A1 | 6/2020 | Winkelman et al. | |

* cited by examiner

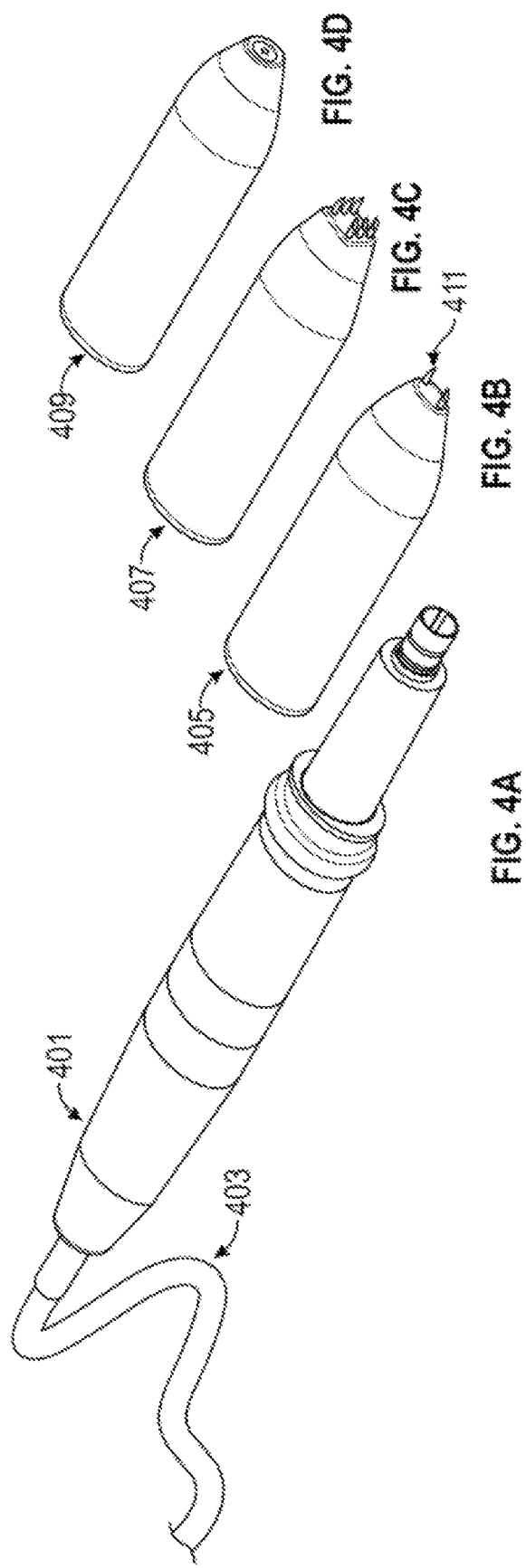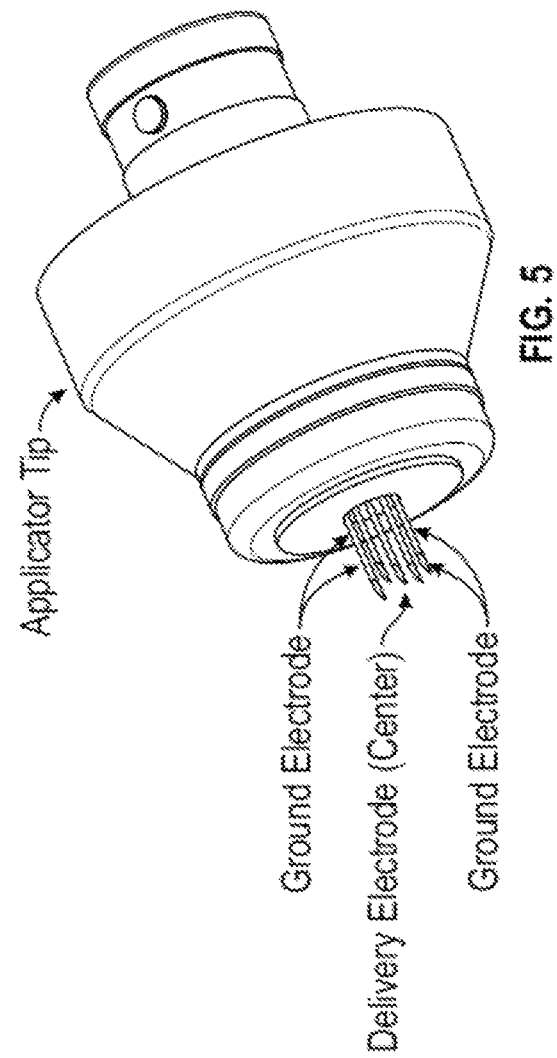

2.5 mm By 2.5 mm Tip with ficucials

Day of Tx
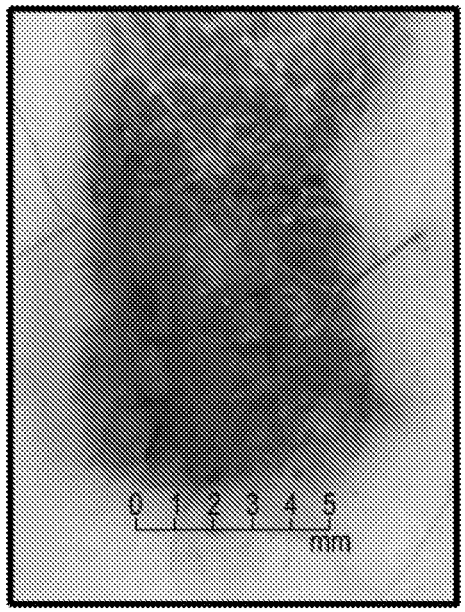
FIG. 11A
1 Day Post Tx
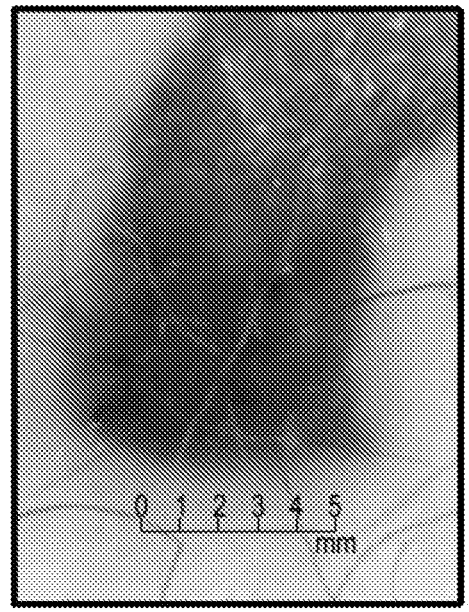
FIG. 11B
Clearance of Ink Observed Earlier Than 90 Days
Post-TX (Photo Not Available)
5 Days Post Tx
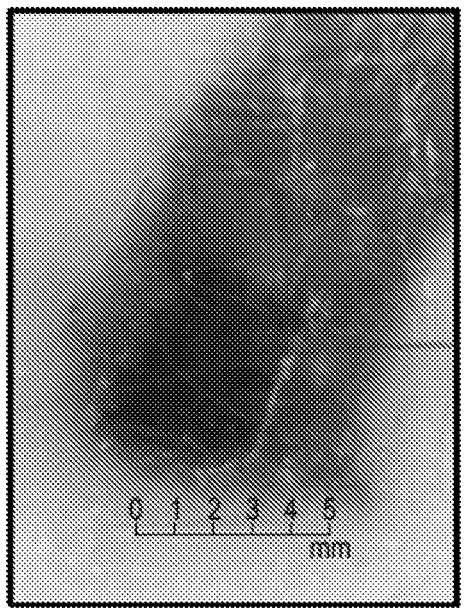
FIG. 11C
90 Days Post Tx
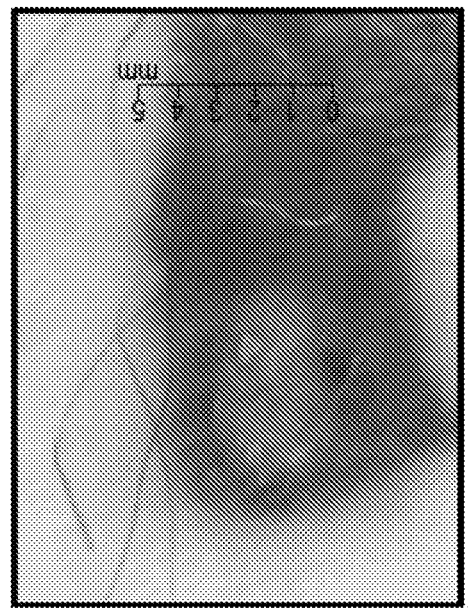
FIG. 11D

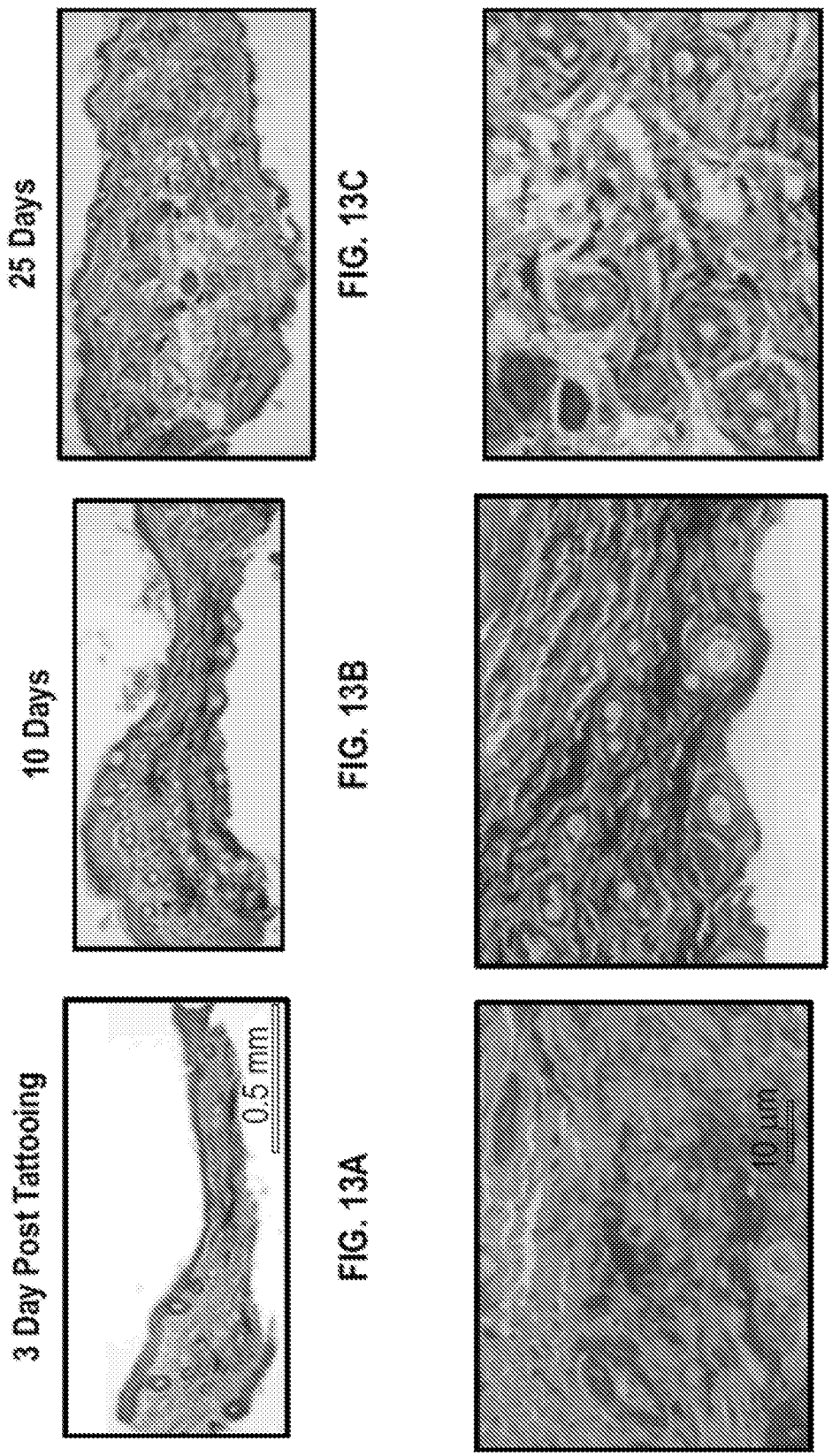

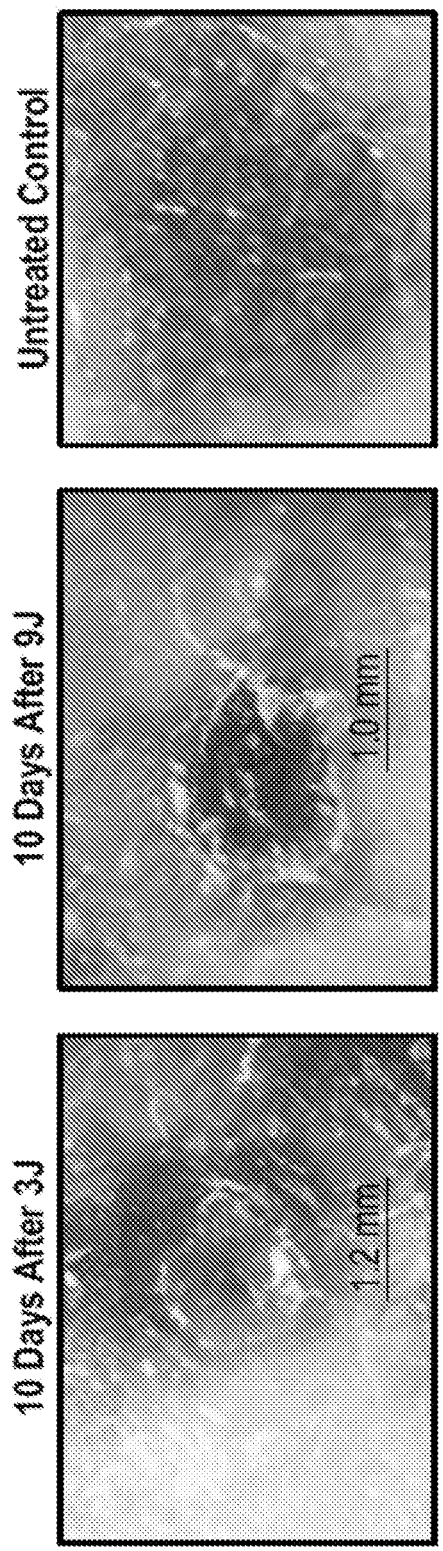

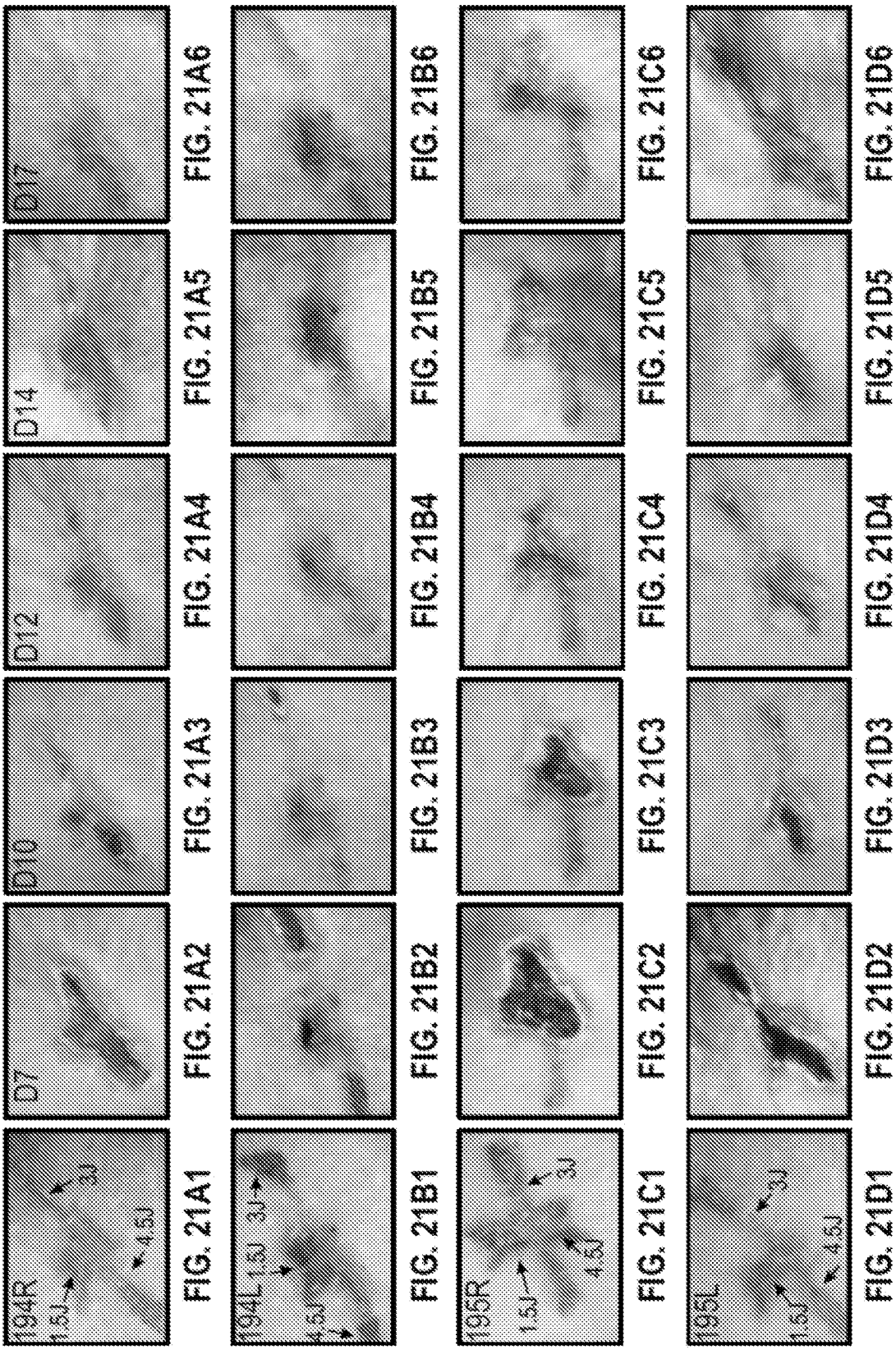

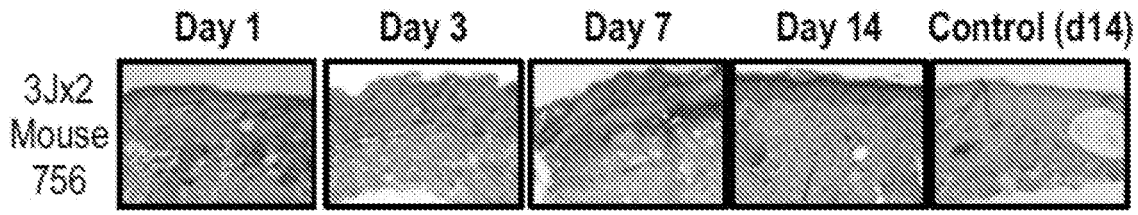
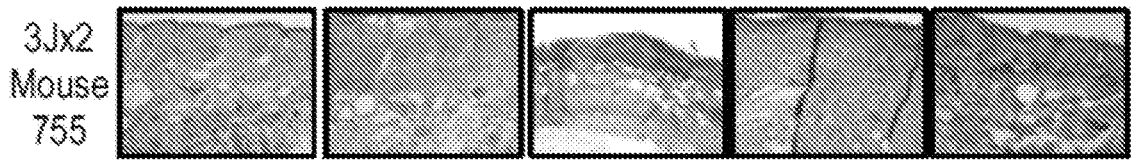
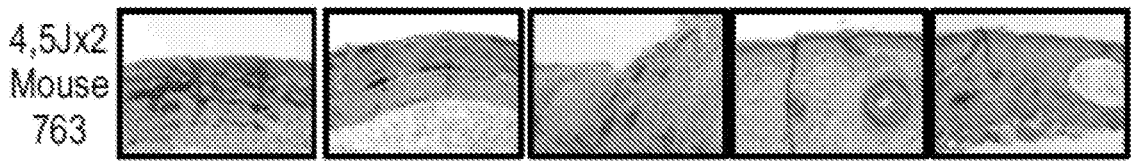
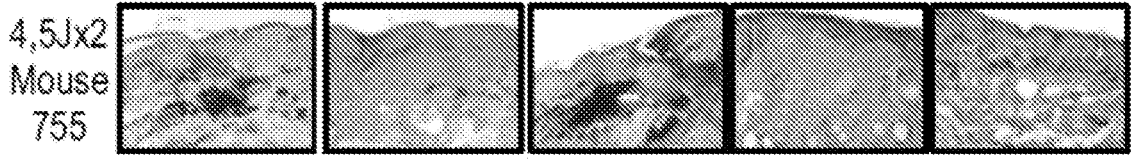
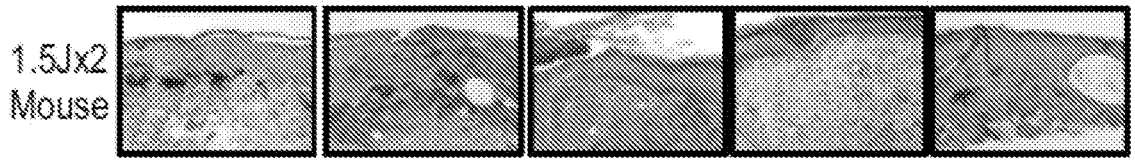
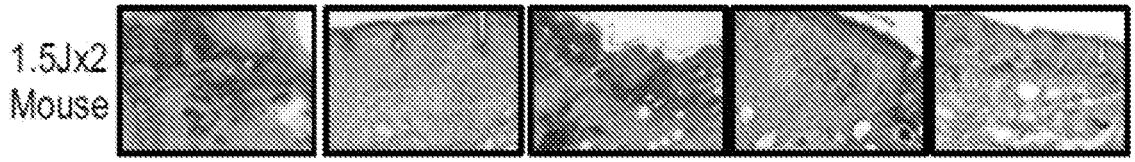

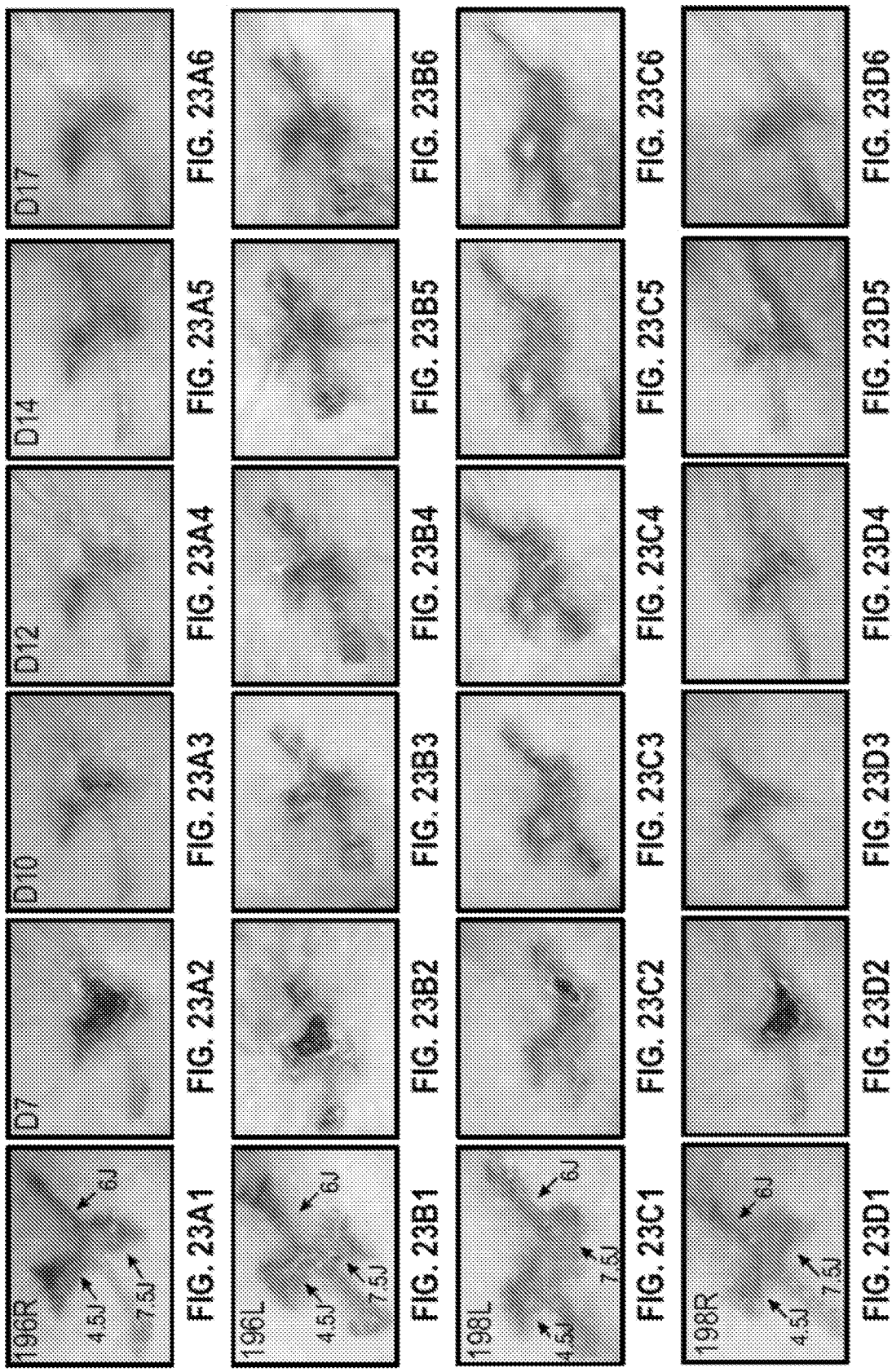

D0 & D7 Treatment Tattoos (1.5, 3, 4.5J) Through Day 14
FIG. 24A1   FIG. 24A2   FIG. 24A3   FIG. 24A4   FIG. 24A5   FIG. 24A6
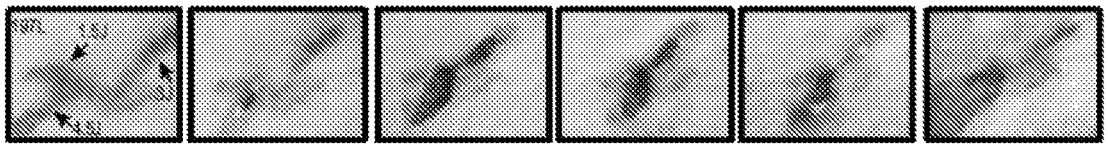
FIG. 24B1   FIG. 24B2   FIG. 24B3   FIG. 24B4   FIG. 24B5   FIG. 24B6
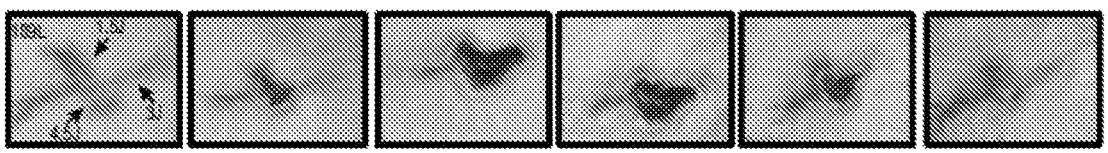
FIG. 24C1   FIG. 24C2   FIG. 24C3   FIG. 24C4   FIG. 24C5   FIG. 24C6
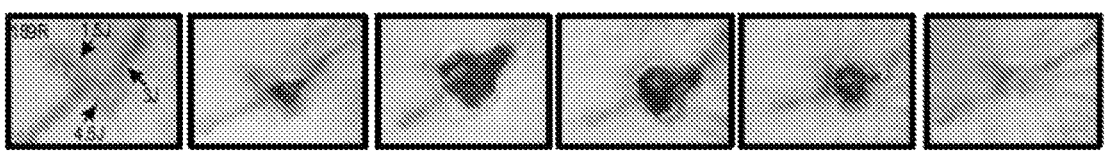
FIG. 24D1   FIG. 24D2   FIG. 24D3   FIG. 24D4   FIG. 24D5   FIG. 24D6
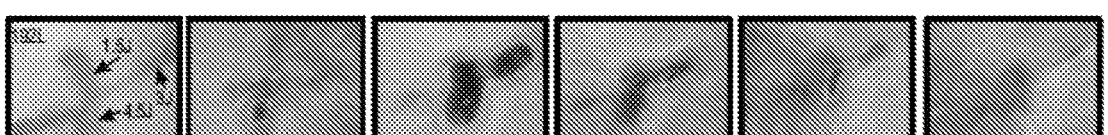
FIG. 24E1   FIG. 24E2   FIG. 24E3   FIG. 24E4   FIG. 24E5   FIG. 24E6
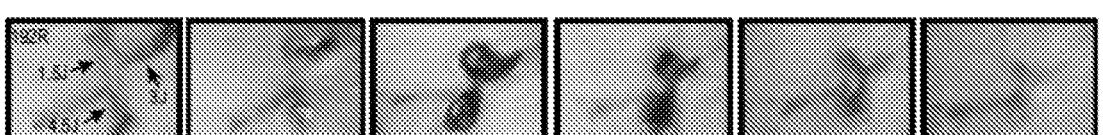
FIG. 24F1   FIG. 24F2   FIG. 24F3   FIG. 24F4   FIG. 24F5   FIG. 24F6
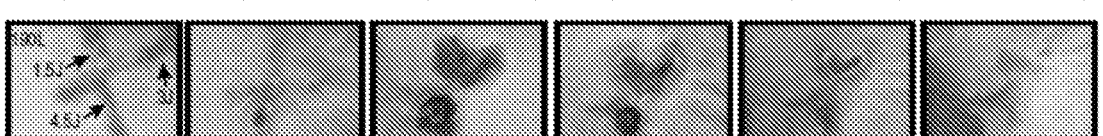
FIG. 24G1   FIG. 24G2   FIG. 24G3   FIG. 24G4   FIG. 24G5   FIG. 24G6
FIG. 24H1   FIG. 24H2   FIG. 24H3   FIG. 24H4   FIG. 24H5   FIG. 24H6

TATTOO REMOVAL

CROSS REFERENCE TO RELATED APPLICATIONS

This patent application is a national phase application under 35 USC 371 of International Patent No. PCT/US2020/023882 filed Mar. 20, 2020, titled "TATTOO REMOVAL," which claims priority to U.S. Provisional Patent Application No. 62/821,959, titled "TATTOO REMOVAL," filed on Mar. 21, 2019 and U.S. Provisional Patent Application No. 62/884,643, titled "TATTOO REMOVAL," filed on Aug. 8, 2019. Each of these provisional patent applications is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

Specifically incorporate by reference in their entirety are each of: U.S. patent application Ser. No. 15/973,254, filed May 7, 2018, which claims priority to U.S. provisional patent application No. 62/542,711, filed Aug. 8, 2017; U.S. patent application Ser. No. 13/631,618 filed Sep. 28, 2012 (now U.S. Pat. No. 9,656,055), U.S. patent application Ser. No. 13/710,077, filed Dec. 12, 2012 (now U.S. Pat. No. 9,956,391); PCT patent application published as WO 2018053539 on Mar. 22, 2018; U.S. patent application Ser. No. 15/920,389, filed on Mar. 13, 2018, which claims priority to U.S. provisional patent application No. 62/618,022, filed on Jan. 16, 2018; and U.S. provisional patent application No. 62/642,552, filed on Mar. 13, 2018. Also incorporated by reference in their entirety are U.S. patent application Ser. No. 16/247,469, titled "TREATMENT TIP WITH PROTECTED ELECTRODES," filed Jan. 14, 2019, and International application no. PCT/US2019/021649, titled "MOVING ELECTRODES FOR THE APPLICATION OF ELECTRICAL THERAPY WITHIN A TISSUE," filed Mar. 11, 2019.

FIELD

This disclosure relates to treatment of tissue by the application of pulsed electric fields, such as nanosecond electrical pulses. More specifically, this disclosure relates to the removal of tattoos by the application of pulsed electric fields, such as nanosecond electrical pulses. These methods and apparatuses may include the use of pulse electric fields in conjunction with the application of one or more non-electrical therapy targeting the affected skin region, such as one or more of: kinetic energy (e.g., vibrational/sonic energy), thermal treatment (e.g., cryotherapy), phototherapy (e.g., the use of light, including laser energy).

BACKGROUND

While tattoos were once considered permanent, it is often desirable to remove tattoos. For example, different types of Q-switched lasers are used to target different colors of tattoo ink depending on the specific light absorption spectra of the tattoo pigments. Successful laser removal can depend on a wide variety of factors including skin color, ink color, and the depth at which the ink was applied. However, treatments tend to be painful and cause scarring. Before the development of laser tattoo removal methods, common techniques included dermabrasion, TCA (Trichloroacetic acid, an acid that removes the top layers of skin, reaching as deep as the layer in which the tattoo ink resides), salabrasion (scrubbing the skin with salt), cryosurgery and excision which is sometimes still used along with skin grafts for larger tattoos.

Unfortunately, none of these techniques has proven to be widely successful. There is a need for effective tattoo removal techniques. Described herein are methods and apparatuses that may address this need.

SUMMARY OF THE DISCLOSURE

The methods and apparatuses (e.g., systems, devices, etc.) described herein generally describe the application of electric energy treatment(s) to skin tissue to alter pigmentation, such as to remove a tattoo. The pulsed electrical energy may be applied as high-field strength, short electrical pulses.

For example, in some variations, described herein are methods and apparatuses for applying a treatment to a tissue to remove a blemish, such as a tattoo. In general, the method may include treating the region of the skin including the pigmentation with an applicator having a plurality of electrodes extending or extendable therefrom and applying the pulsed electrical energy (e.g., high-field strength, short electrical pulses of energy) into the skin. Multiple treatments may be performed by repositioning the applicator relative to the skin region to be treated. As described below, the same region may be partially or entirely treated multiple times, including treating overlapping regions. In some variations, all or most of the skin region may be treated in a single session or in two or more sessions. A topical anesthetic may be applied to the skin prior to treatment.

The methods described herein include in particular, cosmetic methods. These cosmetic methods include cosmetic methods of improving the bodily appearance of a subject (e.g., a subject's skin) by removing or reducing the appearance of a tattoo. For example, the methods described herein include methods of improving the bodily appearance of a subject having a tattoo by applying a plurality of electrodes on or into a subject's skin so that a target region of skin including the tattoo is between two or more of the plurality of electrodes, and applying pulsed electrical energy having a pulse duration in a sub-microsecond pulse range between the two or more of the plurality of electrodes to release the tattoo ink from macrophages within the target region of skin.

The methods and apparatuses described herein may be adapted to apply high-field strength, short electrical pulses by applying a plurality of pulses each having a duration of between 0.1 ns and 1000 ns. For example, applying the treatment may comprise applying the first portion and/or second portion of the pulsed electrical treatment. As mentioned, applying the treatment (e.g., pulsed electrical energy treatment) may comprise applying a plurality of pulses each having a duration of between 0.1 ns and 1000 ns and a peak field strength of at least 1 kV/cm. Applying the treatment may include applying the treatment for less than 10 minutes (e.g., less than 1 second, less than 2 seconds, less than 5 seconds, less than 10 seconds, less than 15 seconds, less than 30 seconds, less than 45 seconds, less than 1 minute, less than 2 minutes, less than 3 minutes, less than 4 minutes, less than 5 minutes, etc.).

The energy density applied to the region of the skin may depend in part on the geometry of the plurality of electrodes. In some variations, the energy density applied to the region of skin (such as a target reason) may be between about 0.03 J/mm$^3$ and about 0.9 J/mm$^3$ for an array of electrodes forming a pattern having a width and a height of between 1.4 mm and 5.5 mm. For example, the energy density applied to the region of skin may be between about 0.03 J/mm$^3$ and about 0.5 J/mm$^3$ for an array of electrodes forming a pattern having a width and a height of between about 4 mm and about 6 mm. In some variations, the energy density applied to the region of skin may be between about 0.06 J/mm$^3$ and about 0.7 J/mm$^3$ for an array of electrodes forming a pattern having a width and a height of between about 2 mm and about 3 mm. In some variations, the energy density applied to the region of skin is between about 0.08 J/mm$^3$ and about 0.9 J/mm$^3$ for an array of electrodes forming a pattern having a width and a height of between about 1 mm and about 2 mm. The pattern of electrodes refers to the arrangement of electrodes in contact with the tissue, and may be any appropriate shape (e.g., a square, rectangle, circle, triangle, etc.), which may be formed by the electrodes, including the space between the electrodes. The dimensions of this pattern may include the electrodes.

Although the examples and illustrations described herein typically relate to the application of pulsed electrical energy in the nanosecond range, in some variation the energy may instead be applied in the picosecond (e.g., between 0.1 ps and 1000 ps) and/or microsecond (e.g., between 1 microsecond and 1000 microseconds) ranges, or other pulse width ranges, including variable pulse width ranges.

In any of the methods described herein, the electrodes may be placed into or against the subject's skin to deliver high-field strength, short electrical pulses to aid in removal of a tattoo. For example, any of these methods may include inserting a plurality of electrodes into a subject's skin so that a region of skin including targeted ink particles is between two or more of the plurality of electrodes. Alternatively, applying the electrodes may include applying non-penetrating electrodes against the skin. For example, in some variations the skin may be pinched or gripped between two or more electrodes on the surface of the skin.

Any of the methods and apparatuses described herein may include or be configured for inserting electrodes into the patient's skin before applying the plurality of electrical pulses. For example, the electrodes may be inserted into the outer layers of skin to a depth of less than 5 mm, less than 4 mm, less than 3 mm, less than 2 mm, between about 1 mm and about 2 mm, etc. The skin may be prepared ahead of time, e.g., washed, shaved, roughened, etc. Alternatively or additionally, the electrical pulses may be applied transdermally, without puncturing the skin. For example, any of these methods may include applying the set of electrodes on the surface of the patient's skin before applying the plurality of short electrical pulses. In such variations one or more conductive or non-conductive gels or other materials may be applied to the skin, including to the electrode contact points and/or the region between them. For example, a non-conductive or lower-conductance gel may be used. Alternatively or additionally, a gel (low-conductance or non-conductive gels) may be used with needle electrodes.

While in some variations a pair of electrodes may be used, in other variations more than two electrodes (e.g., two or more active electrodes and two or more ground electrodes) may be used. The active electrodes may be coupled together; the ground electrodes may be coupled together.

The methods and apparatuses described herein may be configured to minimally disrupt the skin tissue, other than tattoo. For example, applying the electrical energy may include applying a non-thermal treatment that does not disrupt the cell membrane of the epidermal cells. Note that in some variations in which one or more additional or accessory therapies (including cryotherapy, sonic therapy, and/or laser therapy) are applied in addition to the electrical energy, the additional therapy may include the application of thermal energy.

As mentioned, the applied electrical pulses may have any appropriate parameter values (e.g., frequency, pulse width, amplitude, etc.), so long as the energy delivered to the tissue is above the threshold for eliminating the tattoo, including targeting the macrophages within the dermal tissue. For example, applying may comprise applying the pulsed electrical energy between the plurality of electrodes, wherein pulses of the pulsed electrical energy have a peak field strength of at least 0.1 kV/cm (e.g., 1 kV/cm, 5 kV/cm, 10 kV/cm, etc.).

Any appropriate dose parameter may be used for treatment. For example, the methods may include applying a single treatment dose extending for a treatment time (e.g., 20 minutes or less, 15 minutes or less, 10 minutes or less, 5 minutes or less, etc., between 1 second and 20 minutes, between 1 second and 10 minutes, between 1 second and 5 minutes, etc.). For example, the method may comprise applying treatment for less than 5 minutes. In some variations the number of pulses applied during treatment may be between, for example, 10 and 5000 (e.g., between 10-2000, between 10-1500, less than 5000, less than 4000, less than 3000, less than 2000, less than 1000, less than 500, etc.) For example, the method may include applying less than 1000 pulses.

For example, applying the plurality of high-field strength, short electrical pulses may include applying the high-field strength, short electrical pulses for less than a predetermined time (e.g., 1 second or less, 2 seconds or less, 5 seconds or less, 10 seconds or less, 15 seconds or less, 30 seconds or less, 45 seconds or less, 1 minute or less, 2 minutes or less, 3 minutes or less, 4 minutes or less, 5 minutes or less, 10 minutes or less, 15 minutes or less, etc.) and/or for a predetermined number of pulses (e.g., between 2 and 30 pulses, between 2 and 60 pulses, between 2 and 120 pulses, between 2 and 240 pulses, between 2 and 680 pulses, etc.). The pulses may be applied at any appropriate frequency. For example, the plurality of high-field strength, short electrical pulses may be applied between 0.05 Hz and 100 Hz (e.g., between 0.05 Hz and 20 Hz, between 0.05 Hz and 10 Hz, etc.).

Repeated dosing may not be necessary, although in some variations additional (repeated) treatments may be applied to the same region of tissue. In some variations the same region of tissue may not be re-treated until after a waiting period of, e.g., 1 day, 4 days, 7 days, 10 days, 12 days, 14 days, etc. For example, any of these methods may include allowing the region of skin to recover, for example, for 1 week before reapplying electrical energy to the region.

In general, a method as described herein may include: applying a plurality of electrodes on or into a subject's skin so that a target region of skin including a tattoo is between two or more of the plurality of electrodes; and applying pulsed electrical energy having a pulse duration in a sub-microsecond pulse range between the two or more of the plurality of electrodes to release a tattoo ink from macrophages within the target region of skin.

For example, a method may include: applying a plurality of electrodes on or into a subject's skin so that a target region of skin including a tattoo is between two or more of the plurality of electrodes; applying a first pulsed electrical energy having a pulse duration in sub-microsecond pulse range between the two or more of the plurality of electrodes; and applying, after a delay period of greater than 12 hours, a second pulsed electrical energy having a pulse duration in sub-microsecond pulse range to the target region of skin, wherein the first and second pulsed electrical energy causes release of an ink from the tattoo from macrophages within the target region of skin. The delay period may be longer (e.g., greater than 24 hours, greater than 2 days, greater than 3 days, greater than 4 days, greater than 5 days, greater than 6 days, greater than 7 days, etc., or between 2-10 days, between 3-9 days, between 5-8 days, between 5-9 days, between 5-10 days, etc.). The first pulsed electrical energy may be the same or different from the second pulse electrical energy.

In general, when applying pulsed stimulation, the electrical energy applied to the skin may be in the form of one or more electrical pulses. The pulse duration may be at least 0.01 nanoseconds (ns) at the full-width-half-maximum (FWHM). The pulse duration may also be at least 1 ns at FWHM, or the pulse duration may be at least 5 ns at FWHM. The pulse duration may be 1,000 ns or shorter.

As mentioned, the duration of the pulse may be in the range of 0.01 ns to 1,000 ns. The duration of the pulse may also be in the range of 1 ns to 600 ns (e.g., 10 ns to 500 ns, 10 ns to 400 ns, etc.). In some implementations, the duration of the pulses may be in a picosecond ranges, or microsecond ranges, just to name a few. The applied electrical energy per volume of the skin subject to treatment (e.g., between electrodes) may be at least 10 mJ/mm$^3$, or at least 100 mJ/mm$^3$, or at least 1,000 mJ/mm$^3$. The applied electrical energy per volume of the skin treated may also be in the range of 0.1 mJ/mm$^3$ to 10,000 mJ/mm$^3$.

The electrical field produced by each pulse may be at least 1 kV/cm at the peak amplitude of the pulse. The electrical field produced by each pulse may also be at least 10 kV/cm at the peak amplitude of the pulse. The electrical field produced by each pulse may be in the range of 1 kV/cm to 1,000 kV/cm at the peak amplitude of the pulse (e.g., the electrical field produced by each pulse may be in the range of 10 kV/cm to 100 kV/cm, 15 kV/cm to 50 kV/cm, 20 kV/cm to 30 kV/cm, etc.).

The number of electrical pulses during a single treatment may be at least 1. The number of pulses may also be at least 100. The number of pulses may be at least 1,000. The number of pulses may be less than 10,000. For example, the number of pulses may be between 20 and 200, between 30 and 150, between 30 and 100, etc. Pulses may be applied at a frequency of between 1 and 100 Hz, e.g., between 1 and 50 Hz, between 1 and 25 Hz, between 1 and 20 Hz, between 1 and 10 Hz, between 2 and 6 Hz, etc. The treatment time per session may be between 1 second and 60 seconds, between 5 seconds and 30 seconds, between 5 seconds and 20 seconds, etc.

An entire tissue target region may be covered by the applicator including the plurality of electrodes. In some variations, the tissue may be treated by, e.g., dividing the treatment (e.g., treatment dose) into two or more parts, and rotating the applicator tip so that the electrodes apply the energy to the same portion of skin tissue from multiple different rotational orientations during the treatment. Adjacent and/or overlapping regions may be treated in this manner. In some variations, non-overlapping, but adjacent regions may be treated.

For example, described herein are methods of treating a skin tissue by applying pulsed electrical energy (in some examples comprising a plurality of nanosecond electrical pulses having a pulse duration of between 0.1 ns and 1000 ns), wherein the treatment is divided into a different portions in which the same or adjacent regions are treated. The method may include: contacting the tissue with an applicator tip (e.g., treatment tip) having a pattern of electrodes; applying the first portion of the treatment to a region of the tissue over a tattoo; and applying additional portions of the treatment to the same region of the tissue in a new orientation that is rotated relative to the first orientation. The rotation of the pattern of electrodes may be about a line of rotation through the plurality of electrodes (e.g., a midline through the treatment tip and/or though the plurality of electrodes). The same electrodes of the treatment tip may form the pattern of electrodes applied in the first orientation as in the second orientation (for example, by mechanically or electrically activating only certain electrodes of the array of electrodes of the applicator tip); also the pattern may be formed by all of the electrodes of the treatment tip.

Any appropriate type of electrode may be used, including penetrating electrodes (e.g., needle electrodes, blade electrodes, etc.) or non-penetrating electrodes (e.g., surface electrodes). In some variations the treatment tip includes an array of needle electrodes. The electrodes may be fixed relative to the distal face of the treatment tip, or they may be configured to retract relative to the treatment tip (e.g., retract into the treatment tip).

In any of the methods described herein, the movement of the electrodes to different regions (including rotation of the electrodes relative to the different regions) may be performed manually, semi-manually, or automatically. The movement of the electrodes (e.g., movement of the applicator and/or applicator tip) between different target regions of the skin and/or over the same target region of the skin for treatment may be performed robotically. In addition, any or all of the steps of the methods disclosed herein, including moving, removing and/or reapplying the electrodes, as well as coordinating application of the pulsed electrical energy, may be performed by a robotic system, for example, under computer control.

Also described herein are apparatuses (e.g., systems and devices) configured to perform any of these methods. For example, a system may include a pulse generator; an applicator having a plurality of electrodes at a treatment tip of the applicator, the applicator tip configured to apply energy from the pulse generator to the plurality of electrodes; and a controller configured to control, at least partially, operation of the pulse generator and the applicator tip. The controller may comprise a processor having a set of instructions, wherein the set of instructions, when executed by the processor causes the controller to apply the pulsed electrical treatment.

For example, a system for treating tissue may include: a pulse generator; an applicator configured to apply energy from the pulse generator to a plurality of electrodes at a treatment tip of the applicator, and a controller configured to control, at least partially, operation of the pulse generator and the applicator as described herein. The controller may include a processor having a set of instructions, wherein the set of instructions, when executed by the processor, causes the controller to apply the pulsed electrical treatment.

A system as described herein may include: a pulse generator; an applicator having a plurality of electrodes, the applicator configured to apply energy from the pulse generator to the plurality of electrodes; and a controller configured to control, at least partially, operation of the pulse generator, the controller comprising a processor having a set of instructions which, when executed by the processor, causes the application of a pulsed electrical energy having a pulse duration in a sub-microsecond pulse range through the plurality of electrodes to a target region of a skin comprising a tattoo such that the pulsed electrical energy is sufficient to cause a release of a tattoo ink from macrophages within the target region of the skin.

The same or a different controller may be configured to control, as least partially, the operation of the applicator. In some variations multiple controllers may be included as part of the system. The controller may be integrated with the other parts of the system (e.g., the applicator and/or pulse generator, etc.). For example, in some variations the controller (including one or more processors) may be housed within a housing to which all or a portion of the pulse generator is also enclosed. Alternatively, in some variations the controller and/or one or more processors may be remote to the pulse generator.

The applicator may include a set of electrodes and the plurality of electrodes is a subset of the set of electrodes. For example, in some variations, at least some or each electrode of the plurality of electrodes comprises a needle electrode extending or extendable proud of a base of the applicator, further wherein at least some or each needle electrode includes an insulated base portion and uninsulated tip portion. The insulated base portion may extend between at least 0.1 and 1 mm from the base of the applicator. The uninsulated portion may extend between 1 and 3 mm from the base of the applicator.

The set of instructions may further cause a second pulsed electrical energy having a pulse duration in sub-microsecond pulse range to be delivered to the same target region at least 24 hours following the applying pulsed electrical energy.

Any of the systems described herein may be configured to apply (or to coordinate the application of) one or more dye-disrupting therapies. For example, any of these systems may include one or more therapy applicators configured to apply a dye-disrupting therapy to the target region of skin to break up clusters of dye. The dye-disrupting therapy applicators may include one or more of: a sonic transducer, a thermal transducer, and/or a laser-light transducer. The dye-disrupting therapy applicators may be separate or may be attached or integrated with the applicator. The controller may be configured to coordinate the application of the dye-disrupting therapy from the one or more dye-disrupting therapy applicators and the application of the pulsed electrical energy. For example, the controller may be configured to apply the dye-disrupting therapy concurrently with the application of the pulsed electrical energy.

The applicator may be configured so that the plurality of electrodes are configured to be inserted between 1 mm and 3 mm deep into the target region of the skin. The controller may be configured to deliver the pulsed electrical energy at an energy density of between about 0.01 J/mm$^3$ and about 1.5 J/mm$^3$. In some variations, the pulsed electrical energy has a pulse duration between 0.01 nanoseconds and 1000 nanoseconds. The controller may be configured to cause the application of the pulsed electrical energy such that the pulsed electrical energy has a peak field strength of at least 0.1 kV/cm. The controller may be configured to cause the application of the pulsed electrical energy for less than 5 minutes. The controller may be configured to cause the application of the pulsed electrical energy for less than 1000 pulses.

As mentioned, any of these systems may be robotic systems wherein the applicator comprising a treatment tip with an array of electrodes is coupled to a moveable arm. For example, the robotic system may receive instructions from the controller and move one or both of the applicator and the treatment tip to change position relative to the target skin. For example, a system for applying pulsed electrical treatment to tissue may include: a movable arm (e.g., robotic arm); an applicator operatively coupled to the movable arm, the applicator configured to apply pulsed electrical energy from a plurality of electrodes of the applicator; and a processor comprising a set of instructions for executing operations, the set of instructions including instructions for: moving the movable arm to contact a region of tissue with the applicator; directing application of the pulsed electrical treatment to the first region of the tissue; and directing application of subsequent pulsed electrical treatments to the same and/or different regions of tissue.

In some examples, the robotic system may include a navigation interface comprising, for example, an image acquisition device and the navigation interface may be configured to receive imaging data and/or determine a path for treatment (e.g., application of treatment energy) based on the pigmentation (e.g., tattoo). In general, the navigation interface may determine the distance between the tissue (as well as the location of the target treatment site on the tissue) and the plurality of electrodes/treatment tip, and/or the orientation of the plurality of electrodes/treatment tip and the target tissue, to allow control and guidance of the treatment tip relative to the target tissue.

The applicator may be operably connected to the movable arm, such as held by the movable (e.g., robotic) arm. Alternatively, the applicator may be integrated into the movable arm.

For example, a system may include: a movable arm; an applicator having a plurality of electrodes, wherein the applicator is operatively coupled to the movable arm and configured to apply pulsed electrical energy from the plurality of electrodes; and one or more processors comprising a set of instructions for executing operations, the set of instructions including instructions for: moving the movable arm to contact a target region of tissue comprising a tattoo with the applicator; directing application of the pulsed electrical energy to the target region of tissue, wherein the pulsed electrical energy has a pulse duration in a sub-microsecond pulse range and electrical energy sufficient to cause a release of a tattoo ink from macrophages within the target region of the skin.

As mentioned, any of these systems may include a navigation interface comprising an image acquisition device. The navigation interface may be configured to receive imaging data and determine a path for treatment based on the pigmentation of the target region of the skin. The navigation interface may be configured to determine a distance between the tissue and the plurality of electrodes to allow control and guidance of the treatment tip relative to the target tissue. The navigation interface may be configured to determine an orientation of the plurality of electrodes relative to the target tissue to allow control and guidance of the treatment tip relative to the target tissue. The applicator may be integrated into the movable arm or may be separate from the movable arm. A robotic system may include any system features described herein.

A treatment may be an in vivo treatment of the skin of a human comprising at least one treatment session, i.e. administration of the electrical energy to the skin by physician at an office visit. In some variations only one treatment session is needed and/or useful to complete the treatment. In some variations the at least one treatment session may comprise applying electrical energy to the skin multiple times. Thus, the treatment may comprise a plurality of treatment sessions. For example, it may comprise at least two treatment sessions or at least three treatment sessions.

In some variations, the methods described herein may include the concurrent use of one or more additional treatment modalities, such as mechanical (e.g., the use of acoustic energy, e.g., between about 10 Hz and about 5 MHz) and/or optical (e.g., laser light) in conjunction with the application of pulsed electrical energy (e.g., high-field strength, short electrical pulses, including microsecond or sub-microsecond pulses).

Thus, the methods of tattoo removal described herein may including the application of electrical energy to the skin in conjunction with one or more other therapies ("adjunct therapies") and/or pharmaceutical agents. The use of an adjunction therapy and/or a pharmaceutical agent in conjunction with the pulsed electrical stimulation as described herein may result in effects beyond what either treatment alone may achieve. For example, any of these methods may include applying the pulsed electrical energy and concurrently apply a sonic therapy, a cryotherapy and or a laser-based therapy. "Concurrently" in this context is intended to be broadly construed to include, actions that occur within a short period of time (for example, within few days, hours, minutes, or seconds) before or after, the application of the pulsed electrical energy, or at the same time as the application of the pulsed electrical energy.

For example, described herein are methods (e.g., methods of removing a tattoo), that include: inserting a plurality of electrodes into a subject's skin so that a target region of skin including a tattoo is between two or more of the plurality of electrodes; and applying pulsed electrical energy having a pulse duration in sub-microsecond pulse range between the two or more of the plurality of electrodes, wherein the pulsed electrical energy provides an energy density sufficient to release tattoo ink from macrophages (e.g., by disrupting macrophages) within the target region. Any of these methods may include applying a dye-disrupting therapy to the region of skin to break up clusters of dye (e.g., concurrently or within a predetermined period after applying the pulsed electrical energy, such as within a few seconds, minutes, hours, days, etc.). For example, the dye-disrupting therapy is applied concurrently with applying pulsed electrical energy or within 1 month thereafter. Any dye-disrupting therapy may be used, including but not limited to one or more of: a sonic therapy, a cryotherapy and or a laser-based therapy.

In general, inserting may include inserting the plurality of electrodes between 1 mm and 3 mm deep into the subject's skin. The energy density applied to the region of skin may be between about 0.01 J/mm$^3$ and about 1.5 J/mm$^3$. The pulsed electrical energy may provide an energy density sufficient to release the ink (e.g., from the macrophages), in some variations by disrupting them; for example, sufficient energy may be applied to disrupt greater than 80% of the macrophages within the target region. In some variations the pulsed electrical energy may have a pulse duration between 0.01 nanoseconds and 1000 nanoseconds.

Each electrode of the plurality of electrodes may comprise a needle electrode with an insulated base portion and uninsulated tip portion. The method may include inserting the plurality of electrodes such that insulated portions of each of the plurality of electrodes extend between 0.1 and 1 mm below a surface of the skin. The method may include inserting the plurality of electrodes such that an uninsulated portion of each of the plurality of electrodes extends between 1 and 3 mm below a surface of the skin. For example, inserting the plurality of electrodes into the subject's skin may comprise inserting an array of needle electrodes into the skin. The pulses of the pulsed electrical energy may have a peak field strength of at least 0.1 kV/cm (e.g., 0.1 kV or greater, 0.2 kV/cm or greater, 0.3 kV/cm or greater, 0.4 kV or greater, 0.5 kV or greater, 0.7 kV or greater, 1 kV or greater, 2 kV or greater, 5 kV or greater, 10 kV or greater, etc.). Applying the pulsed electrical energy may comprise applying for less than 5 minutes (e.g., 5 min or less, 3 min or less, 2 min or less, 1 min or less, 0.5 min or less, 0.2 min or less, 0.1 min or less, 1 sec or less, etc.). Applying the pulsed electrical energy may comprises applying 1000 pulses or less (e.g., 900 pulses or less, 800 pulses or less, 700 pulses or less, 500 pulses or less, 400 pulses or less, 300 pulses or less, 200 pulses or less, 100 pulses or less, 75 pulses or less, 50 pulses or less, etc.).

Any of these methods may be computer-controlled or performed with a use of robotic system. According to some aspect of the present disclosure, a machine-readable medium is provided. The machine-readable tangible medium may store instructions for causing one or more machines to execute operations for: applying a plurality of electrodes on or into a subject's skin so that a target region of skin including a tattoo is between two or more of the plurality of electrodes; and applying pulsed electrical energy having a pulse duration in a sub-microsecond pulse range between the two or more of the plurality of electrodes to release a tattoo ink from macrophages within the target region of skin.

Further, a method of removing a tattoo may include: inserting a plurality of electrodes into a subject's skin so that a target region of skin including at least a portion of the tattoo is between two or more of the plurality of electrodes; applying pulsed electrical energy having a pulse duration in sub-microsecond pulse range between the two or more of the plurality of electrodes, wherein the pulsed electrical energy provides an energy density sufficient to release captured tattoo ink (e.g., from macrophages within the target region); and applying a dye-disrupting energy to the region of skin to break up dye clusters within the target region. In some variations, the minimum treatment threshold energy is 0.01 J/mm$^3$.

The electrodes (e.g., needle electrodes), such as each needle electrode of the plurality of electrodes may comprise an insulated base portion and insulated tip portion.

Inserting the plurality of electrodes may comprise inserting the electrodes such that uninsulated portions of each of the plurality of electrodes extend between 0.8 mm and 3 mm below a surface of the skin. (e.g., between 0.8 mm and 2.2 mm, between 1 and 3 mm, between 1 mm and 2 mm, etc.).

As mentioned, any dye-disrupting energy (e.g., accessory therapy) may be applied. For example, applying the dye-disrupting energy may comprises one or more of: a sonic therapy, a cryotherapy and or a laser-based therapy.

BRIEF DESCRIPTION OF THE DRAWINGS

The patent or application file contains at least one drawing executed in color. Copies of this patent or patent application publication with color drawings will be provided by the Office upon request and payment of the necessary fee.

The novel features of the apparatuses and methods described herein are set forth with particularity in the claims that follow. A better understanding of the features and advantages of these apparatuses and methods will be obtained by reference to the following detailed description that sets forth illustrative embodiments, in which the principles of the invention are utilized, and the accompanying drawings of which:

FIG. 3A shows a region of skin including a tattoo immediately after the application of high-field strength, short electrical pulses (e.g., 100 pulses of 200 ns, 30 kV/cm, at 6 Hz). FIG. 3B shows the treated and adjacent untreated region 3 months after the treatment. FIG. 3C is an enlarged view of the treatment region.

FIGS. 4A-4D illustrate an example of an applicator hand piece (FIG. 4A) and examples of various electrode tips (FIGS. 4B-4D) for an apparatus for treating skin by delivering electrical pulses as described herein. The tips shown in FIGS. 4B-4D may be attached to the end of the applicator of FIG. 4A. FIGS. 4B and 4C show needle electrodes, while FIG. 4D shows an example of a non-penetrating (plate) electrode. The hand piece shown in FIG. 4A may plug into a generator.

FIG. 5 is an example of another applicator tip with one delivery electrode and four ground electrodes.

FIG. 6A is a front view. FIG. 6B is a top view. FIG. 6C is an enlarged view of the electrodes on the tip. FIG. 6D is a perspective view. FIG. 6E is a side view and FIG. 6F is an enlarged side view of the electrodes on the tip.

FIG. 7A is a front perspective view, while FIG. 7B is a slightly enlarged view of the needle electrodes on the tip.

In FIGS. 8A and 8B, the tip includes a set of fiducials (arranged as a cross) centered on the electrodes. FIG. 8A is a front perspective view, while FIG. 8B is a slightly enlarged view of the electrodes and the set of fiducials.

FIG. 9A shows a pair of needle electrodes extending from an insulated base. FIG. 9B shows a similar pair of needle electrodes having an insulated region of the electrode length near the base of the electrode tip. FIG. 9C shows another pair of needle electrodes, similar to that shown in FIG. 9A, with a longer length of insulated region (approximately half of the length). FIG. 9D shows another pair of needle electrodes with the majority of the length insulated, except for the distal tip.

FIGS. 11A-11D illustrate one example of a single treatment of human skin showing removal of a portion of a tattoo. FIG. 11A shows the skin including a treated portion of the tattoo immediately after treatment. FIGS. 11B, 11C and 11D show the same region of skin 1 day, 5 days and 90 days post-treatment, respectively.

FIG. 12A illustrates tattooing a test animal; FIG. 12B shows five tattooed mice.

FIGS. 13A-13F illustrate the time course for the ink encapsulation following tattooing in a test animal (mouse). FIGS. 13A-13C shows sections through tattooed skin 3 days, 10 days and 25 days post-tattooing, respectively; FIGS. 13D-13F show enlarged views of the same skin regions as FIGS. 13A-13C, respectively.

FIGS. 16A-16F show enlarged views of the treated (FIGS. 16A and 16B) and control (FIG. 16C) images of the surface of the skin, and below the surface sections through the treated skin regions taken ten days after treatment with high-field strength, short electrical pulses (delivering 3 J in FIG. 16D and 9 J in FIG. 16E) or untreated (FIG. 16F).

FIG. 17A is a 400× magnification, while FIG. 17B is a 1000× magnification image.

FIGS. 21A1-21A6 show images of a tattooed region of a skin of one mouse prior to treatment (FIG. 21A1) and after 7, 10, 12, 14 and 17 days following two treatments, separated by 24 hours, with high-field strength, short electrical pulses. Three adjacent regions (indicated by (white) arrows in FIG. 21A1) were treated with 1.5 J, 3 J and 4.5 J of energy. FIGS. 21B1-21B6, 21C1-21C6 and 21D1-21D6 show similar results for three other animals, respectively.

FIGS. 22A1-22F5 show histological section through treated tattooed mouse skin on different mice (FIGS. 22A1-22A4, 22B1-22B4, 22C1-22C4, 22D1-22D4, 22E1-22E4 and 22F1-22F4) at various times post-treatment (1 day, 3 days, 7 days, or 14 days, respectively) or control (FIG. 22A5, 22B5, 22C5, 22D5, 22E5, 22F5) skin at 14 days.

FIGS. 23A1-23A6 show images of a tattooed region of a skin of one mouse prior to treatment (FIG. 23A1) and after 7, 10, 12, 14 and 17 days following a single treatment with high-field strength, short electrical pulses. Three adjacent regions (indicated by the arrows in FIG. 23A1) were treated with 4.5 J, 6 J and 7.5 J of energy. FIGS. 23B1-23B6, 23C1-23C6, and 23D1-23D6 show similar series of images for three other animals, respectively.

FIGS. 24A1-24A6 show images of a tattooed region of a skin of one mouse prior to treatment (FIG. 24A1) and after 7, 10, 12, 14 and 17 days following a first treatment with high-field strength, short electrical pulses; a second treatment at approximately the same energy level was given at day 7. Three adjacent regions (indicated by the white arrows in FIG. 24A1) were treated with 1.5 J, 3 J and 4.5 J of energy. FIGS. 24B1-24B6, 24C1-24C6, 24D1-24D6, 24E1-24E6, 24F1-24F6, 24G1-24G6, and 24H1-24H6 each show similar series of images for seven other animals, respectively.

DETAILED DESCRIPTION

Figure 1:
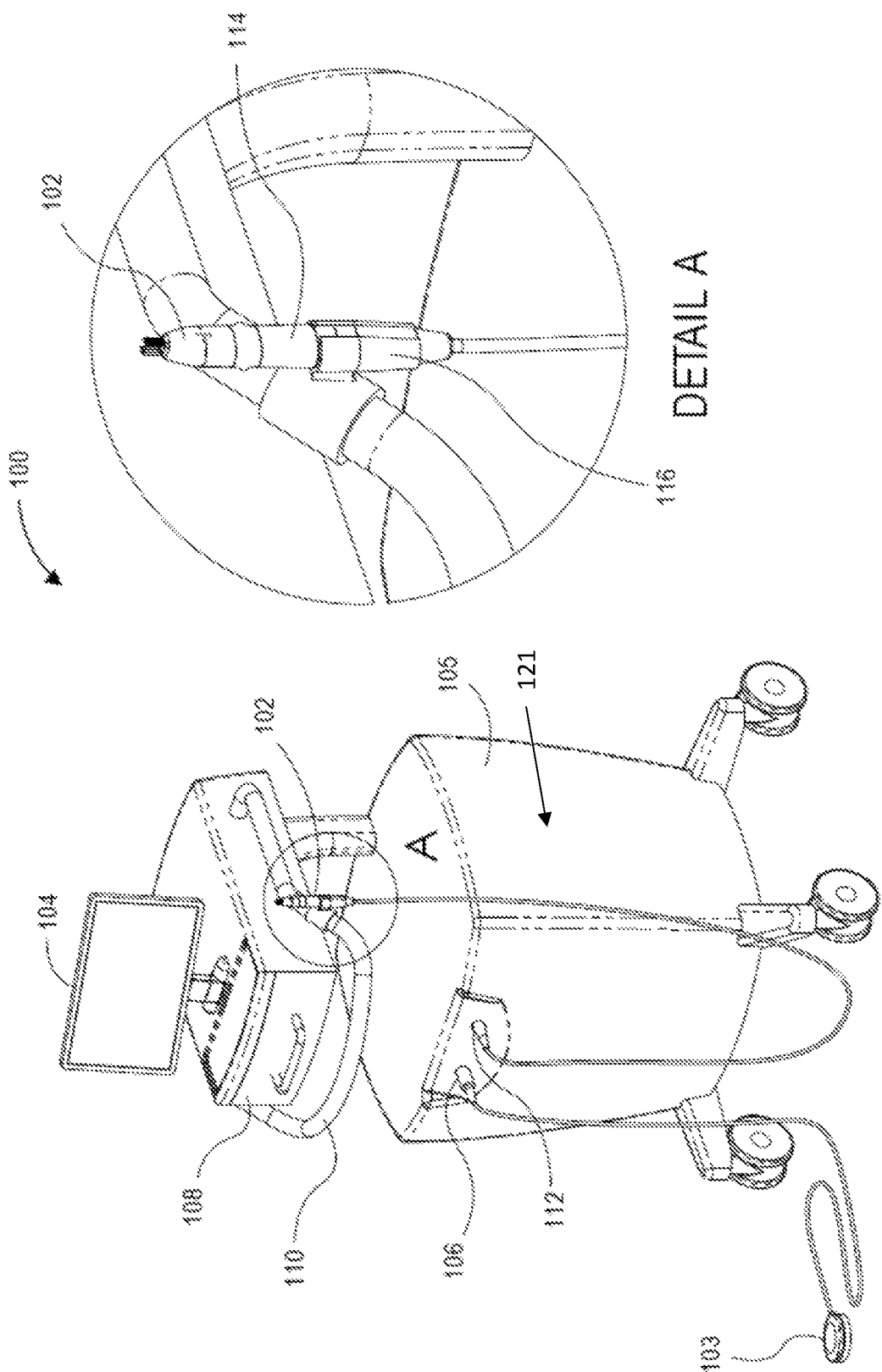
FIG. 1 is an example of a system for generation and delivering electrical pulses, e.g., pulses in the nanosecond range.

In general, described herein are methods and apparatuses for treating skin to remove or reduced tattoos. Tattoo ink is at least partially retained in the dermis because is held by macrophages. The methods and apparatuses described herein may allow the release of tattoo ink from macrophages, allowing the liberation of the ink and clearance of the tattoo; in addition, an agent or therapy for disrupting (e.g., breaking up) ink particles may be used in conjunction with the application of electrical energy. Examples of these accessory therapies may include, but are not limited to thermal (e.g., cryotherapies), optical (e.g., laser-base therapies), sonic, and the like. Such accessory therapies may provide a mechanical shockwave to disrupt the ink particles.

The methods described herein may also allow modification of such adjunct therapies, including the use such therapies at lower-than-expected energy levels. For example, laser tattoo removal may require multiple treatments, as each color of tattoo ink may require a different wavelength laser to release the ink from the fibroblast and macrophage cellular structures that keep the ink localized in the tattoo. Such lasers may result in an intense heating of the ink in the cellular structures necessary to kill the cells and releases the ink, as well as disrupting the ink, but may also result in heating up dermal collagen surrounding the ink and may lead to scarring, especially when multiple sessions are required to treat several colors. The methods described herein may permit the use of lower-energy.

In general, described herein are methods and apparatuses for treating skin tissue to eliminate or reduce tattoos. In particular, the methods and apparatuses (e.g., devices, systems, etc.) described herein may release tattoo ink from macrophages within a targeted region of the dermis, by applying pulsed (e.g., very short pulses) electric treatment to the target region of the tissue. Concurrently or thereafter, the ink may be further broken down (e.g., by the application of an adjunct therapy) so allow the body to clear the ink. The methods described herein may stimulate dermal turnover, helping reduce or eliminate the ink from the dermis.

The methods and apparatuses described herein may be used to treat skin tissue by generally applying a treatment, e.g., a pulsed electrical treatment, to the skin to release the ink held in the tissue, e.g., by macrophages. In some variations, the macrophages may be disrupted or destroyed; e.g., all or some of the macrophages containing ink within a treatment zone (e.g. target region) of the skin may be disrupted or destroyed. Without being bound by a particular theory of operation, the macrophages may be eliminated by destroying the nuclei (e.g., de-nucleating) the cells. Other methods of making the macrophage within the target skin region non-viable may occur, including disrupting or destroying other organelles in the cells, such as the endoplasmic reticulum, mitochondria, etc., or by disrupting the outermost cell membrane (e.g. plasma membrane). Alternatively, in some variations macrophages may be disrupted, and may release tattoo ink, but may not be destroyed. The non-thermal treatment employed in the methodology of the present disclosure is typically an electrical treatment (e.g., very short, high-field strength electric pulses, typically in the sub-microsecond range) adapted to de-nucleate macrophages. These pulses may affect the macrophage cells without provoking an inflammatory response (e.g., without increasing the density of leukocytes and/or melanocytes above a threshold percentage compared to untreated skin). The methods and apparatuses described herein may selectively eliminate the macrophages in the tissue without irrevocably destroying the overlying and/or adjacent tissue, including the epidermis and dermis. The disruption of the macrophages may be specific and effective; unlike the adjacent tissues, the macrophages may not recover within a recovery period (e.g., 1 week, one month, two months, three months, etc.).

Illustrative embodiments are now discussed. Other embodiments may be used in addition or instead. Details which may be apparent or unnecessary may be omitted to save space or for a more effective presentation. Conversely, some embodiments may be practiced without all of the details which are disclosed.

In any of the methods described herein, the pulsed electrical treatment may be nanosecond electric pulsed treatment, which may include the application of electrical pulses with duration of 1,000 nanoseconds (ns) or less. Although the examples described herein focus primarily on pulses having a width (pulse width) within the nanosecond range, other pulse widths may be used. For example, in some variations, pulses may have pulse widths in picosecond ranges, microsecond ranges, or millisecond ranges, just to name a few.

The pulsed electrical treatment may be achieved by providing electrical energy to the target skin region in a form of one or more electrical pulses. Further, these methods may be generally non-thermal, and may be configured to prevent a substantial inflammatory response.

Although in some variations, the treatment of the skin may result in the destruction of the macrophages. That is, the treatment may induce destruction of at least 10%, 20%, 30%, 60%, 70%, 80%, 90%, or more than 90% macrophages, and specifically ink-containing macrophages.

The treatment may comprise at least one treatment session. For example, the treatment session may comprise an administration of the electrical energy to the skin region of a human by physician at an office visit. The treatment of a skin region may also comprise a plurality of treatments sessions. For example, it may comprise at least two treatment sessions or at least three treatment sessions. These treatments may be combined with any other type of treatment modalities to increase efficacy of the treatment. These other treatment modalities may include over-the-counter treatment products, treatments with prescription medicines, surgery, and any of the adjunctive therapies described herein.

Any system suitable for delivery of electrical pulses with the target energy level may be used. A pulse generator may be any pulse generator that is capable of generating pulses, for example, with a duration of 1,000 ns or less. The pulse delivery device may be any device that can deliver electrical pulses to the skin. This device may have an applicator tip that may comprise at least one pair of delivery electrodes. In some embodiments, additional delivery electrodes may be electrically floating and may be switched to become active, as desired. This applicator may comprise at least one ground electrode. The delivery electrode and/or the ground electrode may penetrate into the skin to deliver the electrical pulses to the target skin region to be treated.

For example, a nanosecond pulse generator system such as those shown and described in US2017/0245928A1 (U.S. patent application Ser. No. 15/148,344, titled "HIGH-VOLTAGE ANALOG CIRCUIT PULSER WITH FEEDBACK CONTROL"), which is incorporated herein by reference in its entirety, may be used. The pulse generator system may provide pulses having a duration of 1,000 ns or less to the skin. The system may comprise a power supply, a controller, a pulse generator, and a pulse delivery device (e.g., a wand, or treatment applicator). An example of this system is schematically shown in FIG. 1. FIG. 1 illustrates one example of a nanosecond pulse generator system (NsPEF system) 100. The pulse generator system 100 includes electrode (treatment tip) 102, footswitch 103, and interface 104. Footswitch 103 is connected to housing 105 and the electronic components therein through connector 106. Electrode (e.g., treatment tip 102) in this example is connected to housing 105 and the electronic components therein through high voltage connector 112. NsPEF system 100 also includes a handle 110 and storage drawer 108. As shown in DETAIL A portion of FIG. 1, nsPEF system 100 also includes holster 116, which is configured to hold electrode (treatment tip) 102 at its handle portion 114.

A human operator may input a number of pulses, amplitude, pulse duration, and frequency information, for example, into a numeric keypad or a touch screen of interface 104, and/or some or all of these parameters may be automatically determined based on a target treatment protocol. In some embodiments, the pulse width can be varied. A microcontroller sends signals to pulse control elements within nsPEF system 100. In some embodiments, fiber optic cables allow control signaling while also electrically isolating the contents of the metal cabinet with nsPEF generation system 100, the high voltage circuit, from the outside. In order to further isolate the system, system 100 may be battery powered instead of from a wall outlet.

The applicator may include or be coupled to a treatment tip 102 having two or more (e.g., a plurality) of electrodes. The system may generally include a controller 121. The controller may control operation of the system, and may include one or more processors, one or more memories, and the like. The controller may include logic (e.g., hardware, software, firmware) including instructions that, when executed by the one or more processor(s), may control the system to apply the electrical therapy as described herein. For example, the set of instructions may operate a robotic actuator (e.g., robotic arm) to move the treatment electrodes to the target tissue region and/or control the application of pulsed electrical energy treatment to the tissue. The set of instructions may include instructions controlling the application of the pulses, movement of electrodes applying the energy, and/or placement of the applicator on/off of the tissue. In some variations, the applicator may control the application of pulsed electrical energy to cause the elimination (e.g., de-nucleation) of macrophages within the target skin tissue.

The electrical energy may be applied to the skin in the form of at least one electrical pulse. For example, between 1 and 10000 pulses may be applied (e.g., between 30 and 1000). In one embodiment, at least 10 pulses, at least 100 pulses, at least 1000 pulses, or at least 2000 pulses may be applied to treat the skin during a single treatment. The duration of one or more of the pulses may be in the range of 0.01 ns to 1,000 ns. For example, the pulse width may be between 50 and 500 ns (e.g., between 200 and 300 ns). The duration of one or more of the pulses may be, for example, in sub-microsecond range.

The total estimated energy density applied per volume of the skin being treated may be at least 0.01 J/mm$^3$ (e.g., at least 0.02 J/mm$^3$, at least 0.03 J/mm$^3$, at least 0.04 J/mm$^3$, at least 0.05 J/mm$^3$, at least 0.06 J/mm$^3$, at least 0.07 J/mm$^3$, etc.). In another embodiment, the total applied electrical energy per volume of the treated skin may be in the range of, e.g., between about 0.01 J/mm$^3$ and about 1.5 J/mm$^3$ (e.g., between about 0.02 J/mm$^3$ and about 1.0 J/mm$^3$, between about 0.03 J/mm$^3$ and about 0.9 J/mm$^3$, etc.).

The electrical field produced by each pulse may be at least 0.1 kV/cm (e.g., at least 1 kV/cm, etc.) at the peak amplitude of the pulse. For example, the electrical field may be between 1 and 50 kV/cm (e.g., between 20 to 30 kV/cm). In another embodiment, the electrical field produced by each pulse may be in the range of 0.1 kV/cm to 1,000 kV/cm (e.g., between 0.1 kV/cm and about 100 kV/cm, etc.) at the peak amplitude of the pulse. Yet, in another embodiment, the electrical field produced by each pulse may be in the range of 1 kV/cm to 100 kV/cm at the peak amplitude of the pulse.

The treatment may comprise at least one treatment session, i.e. administration of the electrical energy to the target skin region by physician at an office visit. This treatment session may comprise at least one application of the electric energy to the target skin region. The electrical energy may be delivered to the skin in any manner suitable for the target skin region. For example, the electrical energy may be delivered after penetrating the target skin region by electrodes of the applicator tip. The electric energy may be delivered after insertion of the electrodes into the skin. For example, one application may comprise first penetration of the target skin region by the electrodes of the applicator tip and then delivery of a desirable number of pulses, for example, between 30-1000 pulses, with a pulse duration of between about 100 to 600 ns. More than one application may be used per treatment session to treat the target skin region (e.g., the region including the tattoo). The number of applications may depend on the size of the target skin region. Larger regions may require more than one application per treatment session, as discussed in detail below. The treatment of the target skin region may also comprise a plurality of treatment sessions. For example, it may comprise at least two treatment sessions or at least three treatment sessions. These treatment sessions may also be separated in time by 1 or more days (e.g., 2 days, 3 days, 4 days, 5 days, 6 days, 7 days, etc.).

Although many of the variations described herein refer to the insertion of tissue-penetrating electrodes, such as needle electrodes, into the skin, any appropriate electrode may be used. For example plate electrodes may be used. Tissue including the tattoo may be placed between two plate electrodes. In some variations non-penetrating electrodes, including surface electrodes, may be used.

Figure 2A:
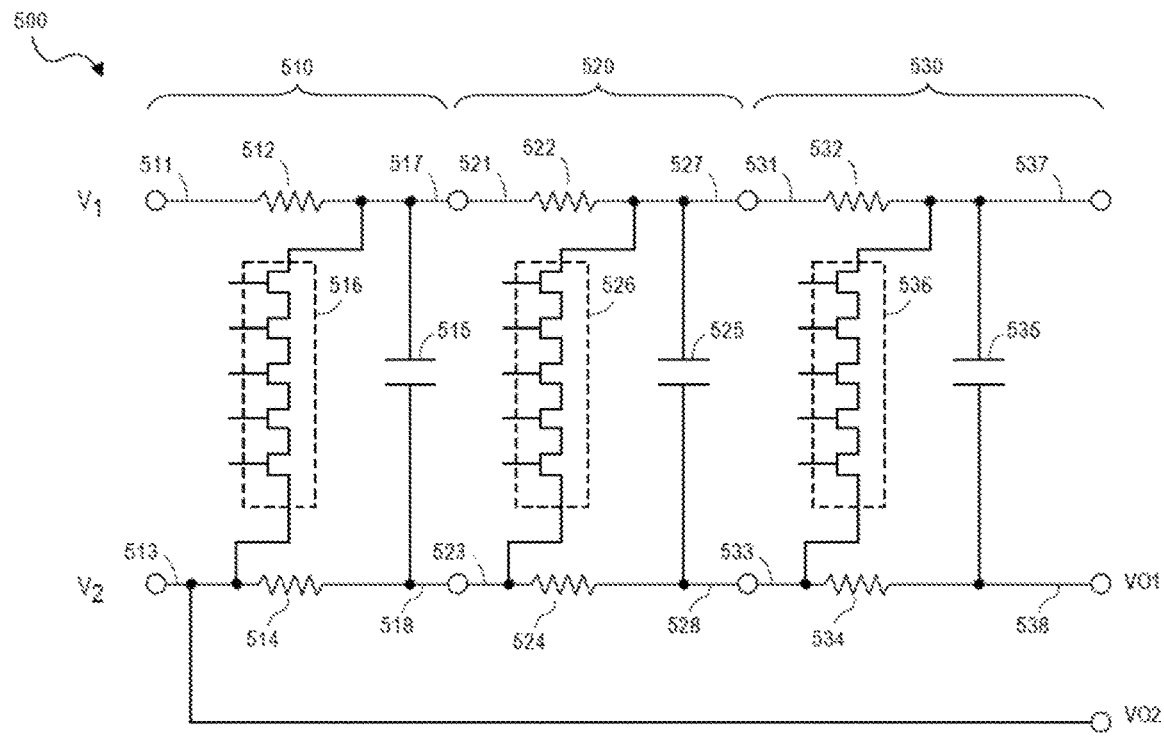
FIG. 2A is an electrical schematic of one example of a pulse generator.
Figure 2B:
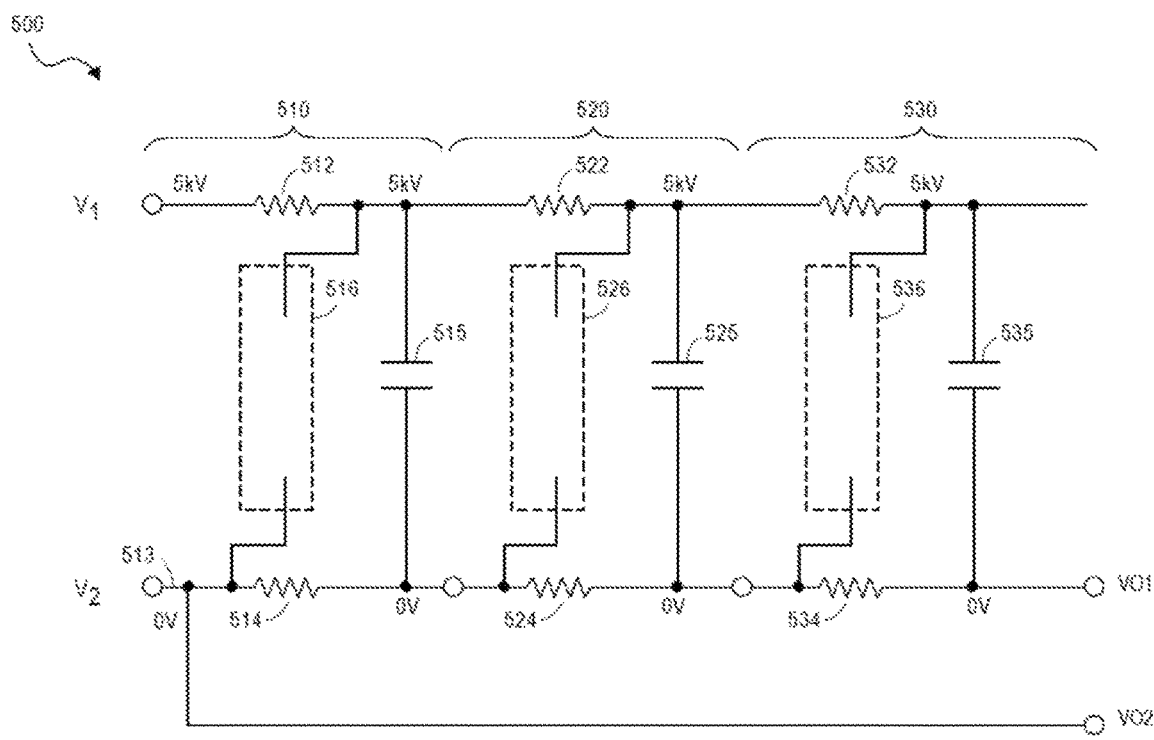
FIG. 2B schematically illustrates the pulse generator of FIG. 2A during a charge mode.
Figure 2C:
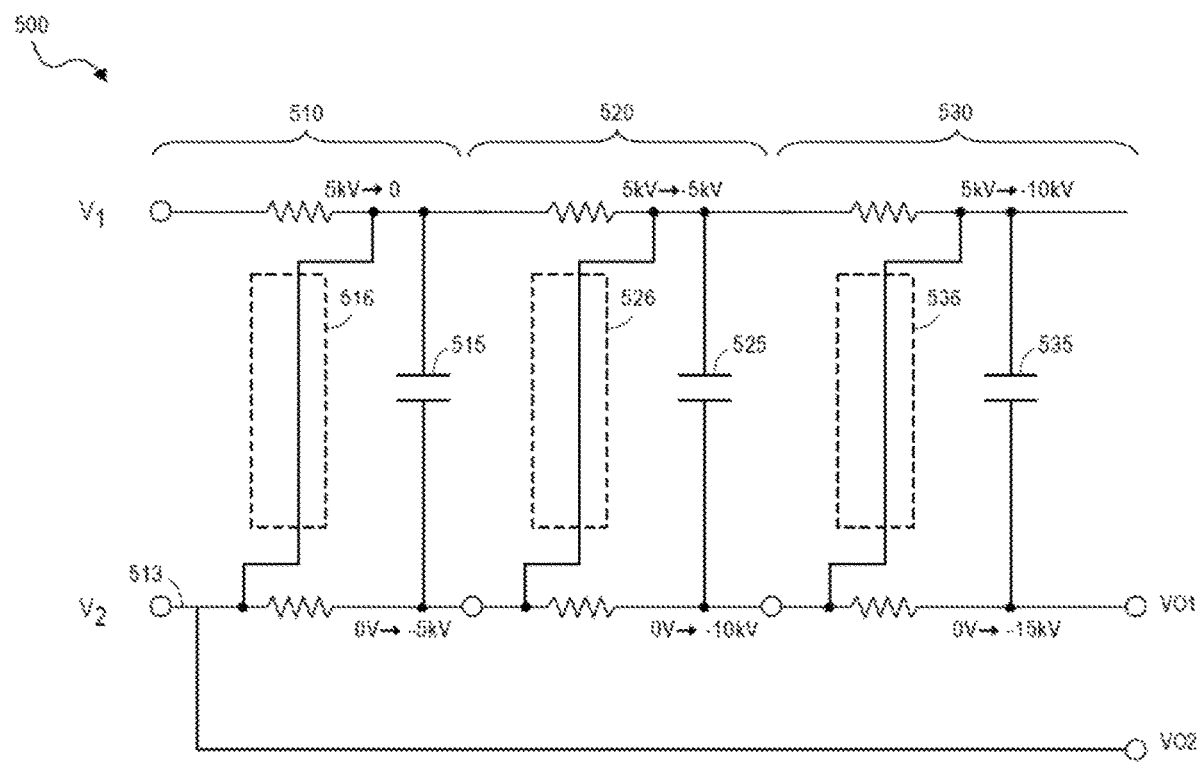
FIG. 2C schematically illustrates the pulse generator of FIG. 2A during a discharge mode.

As stated above, an electrical pulse generation and delivery system is schematically shown in FIG. 1 and includes a pulse generator. An example of the pulse generator is schematically shown in FIGS. 2A-2C. FIG. 2A illustrates a pulse generator circuit 500 which may be used inside nsPEF system 100 such as the one shown in FIG. 1. Pulse generator circuit 500 may illustrate a panel comprising a Marx generator switched by three switch stacks. This example of a nsPEF system can have a single pulse generator circuit panel. In some embodiments, a nsPEF system includes multiple panels in parallel.

Circuit 500 includes three stages, 510, 520, and 530. In some embodiments, another number of stages is used. For example, in some embodiments, 2, 4, 5, 6, 7, 8, 9, or 10 stages are used. Stage 510 includes resistors 512 and 514, capacitor 515, and switch stack 516. Likewise, stage 520 includes resistors 522 and 524, capacitor 525, and switch stack 526, and stage 530 includes resistors 532 and 534, capacitor 535, and switch stack 536. Each of these elements have structure and functionality which is similar to the corresponding elements of stage 510.

Stage 510 has first and second voltage input terminals 511 and 513 and first and second voltage output terminals 517 and 518. Stage 520 has first and second voltage input terminals 521 and 523, and first and second voltage output terminals 527 and 528. Stage 530 has first and second voltage input terminals 531 and 533, and first and second voltage output terminals 537 and 538.

The first and second voltage input terminals 511 and 513 of stage 510 are respectively connected to first and second power supply input terminals $V_1$ and $V_2$. The first and second voltage output terminals 517 and 518 of stage 510 are respectively connected to the first and second voltage input terminals 521 and 523 of stage 520. The first and second voltage output terminals 527 and 528 of stage 520 are respectively connected to the first and second voltage input terminals 531 and 533 of stage 530. The second voltage output terminal 538 of stage 530 and second voltage input terminal 513 of stage 510 are respectively connected to first and second power output terminals VO1 and VO2.

The exemplary pulse generator circuit 500 shown in FIG. 2A operates in a charge mode and in a discharge mode. During the charge mode, described below with reference to FIG. 2B in more detail, capacitors 515, 525, and 535 are charged by current received from the first and second power supply input terminals $V_1$ and $V_2$. During the discharge mode, described below with reference to FIG. 2C in more detail, capacitors 515, 525, and 535 are discharged to provide a current to a load (not shown) connected across first and second power output terminals VO1 and VO2.

FIG. 2B illustrates pulse generator circuit 500 during charge mode. First and second input voltages are respectively applied to first and second power supply input terminals $V_1$ and $V_2$ while each of switch stacks 516, 526, and 536 are nonconductive or open, and while first and second power output terminals may be disconnected from the load (not shown). Because each of switch stacks 516, 526, and 536 are open, substantially no current flows therethrough, and they are represented as open circuits in FIG. 2B. During the charge mode, each of capacitors 515, 525, and 535 are charged by current flowing through resistors 512, 522, 532, 534, 524, and 514 to or toward a voltage equal to the difference between the first and second input voltages.

Each of the switches of switch stacks 516, 526, and 536 has a breakdown voltage rating which should not be exceeded. However, because the switches are serially connected, the capacitors 515, 525, and 535 may be charged to a voltage significantly greater than the breakdown voltage of the individual switches. For example, the breakdown voltage of the switches may be 1 kV, and the capacitors 515, 525, and 535 may be charged to a voltage of 5 kV, when 5 or more switches are used in each switch stack.

For example, the first and second input voltages may respectively be 5 kV and 0 V. In such an example, each of the capacitors 515, 525, and 535 is charged to or toward a voltage equal to 5 kV. In some embodiments, the difference between the first and second input voltages is limited to be less than 10 kV.

FIG. 2C illustrates pulse generator circuit 500 during discharge mode. First power supply input terminal $V_1$ may be disconnected from the first input voltage. In some embodiments, first power supply input terminal $V_1$ remains connected to the first input voltage. Second power supply input terminal $V_2$ remains connected to the second input voltage. In addition, each of switch stacks 516, 526, and 536 are conductive or closed. Because each of switch stacks 516, 526, and 536 are closed, current flows therethrough, and they are represented as conductive wires in FIG. 2C. As a result, a low impedance electrical path from power supply input terminal $V_2$ to power output terminal VO1 is formed by switch stack 516, capacitor 515, switch stack 526, capacitor 525, switch stack 536, and capacitor 535. Consequently, the difference between the voltages at the power output terminals VO1 and VO2 is equal to the number of stages (in this example, 3) times the difference between the first and second input voltages. Where the first and second input voltages are respectively 5 kV and 0 V, a voltage difference of 15 kV is developed across the power output terminals VO1 and VO2.

Other examples of pulse generators and systems that may be used with any of the methods of the present disclosure and/or may be modified to form any of the apparatuses described herein are shown and described in co-pending U.S. patent publication no. 20180078755, U.S. patent publication no. 20170326361, U.S. patent publication no. 20170246455, U.S. patent publication no. 201802433558, and U.S. patent publication no. 20170319851; each of these patent application is herein incorporated by reference in its entirety.

The electrical pulses may be delivered to a target skin region by using applicator tips comprising one or more delivery electrode(s) and at least one ground electrode. For example, needle electrodes may be constructed by using a 30 gauge needle (i.e. about 0.255 mm in diameter). The delivery and the ground electrodes may have the same length for each applicator tip. This length may be varied, for example, in the range of about 1 millimeters (mm) to 5 mm. The electrodes may be arranged to form an open pattern (in these examples, shown as a square pattern, though other shapes may be used). The needle electrodes may be embedded in an insulator (e.g., a Teflon insulation). Any appropriate, preferably biocompatible, electrical insulator may be used, such as, for example, polyvinyl chloride (PVC), polyethylene (PE), PEEK, polyimide, neoprene, rubber, thermoplastic elastomers, and/or conformal coatings like Parylene.

The tip configuration may vary, as described in FIGS. 4A-8B, below. There applicator tip configurations may be suitable for the treatment of the target skin region as described herein. These configurations may include tips comprising at least one delivery electrode and at least one ground electrode.

Each pulse may include a carrier frequency. For example, a pulse may contain significant frequency components centered at about 142.9 megahertz (MHz), and each pulse with a duration of about 14 ns contained significant frequency components centered at about 71.4 MHz. Electrical nanosecond pulses with different amplitudes (e.g., peak amplitude of about 7.0 kilovolts (kV), peak amplitude of about 5.5 kV, etc.) may be used.

Values of the pulse durations and the peak amplitudes referred to herein may be average values unless specifically noted. These pulse durations and the peak amplitudes may vary with a standard deviation of, e.g., 10% of their average values. In general, the skin impedance values may be related to the design of the electrode being used. The target skin region resistance may be expected to be, depending on the size of the target skin region and/or electrodes, and any insulation on the electrodes, between about 10 and greater than about 700 Ohms. For example, see the electrodes shown in FIGS. 6A-8B, described in detail below. Different electrode designs may register different tissue impedances, e.g., between about 100 Ohms and 1 KOhm (e.g., from 150 Ohms to 800 Ohms), depending on the quality of the electrode contact, which may be (in part) a function of the electrode design.

Figure 3A:
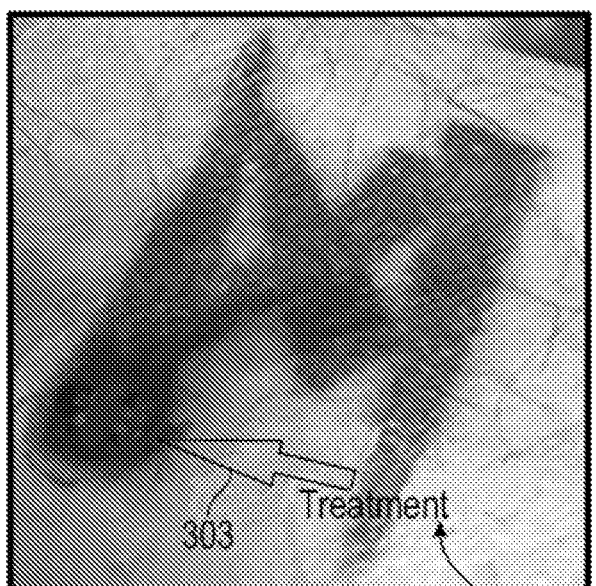
FIGS. 3A-3C illustrate one example of a treatment of a tattoo by the application of high-field strength, short electrical pulses.
Figure 3B:
Figure 3C:
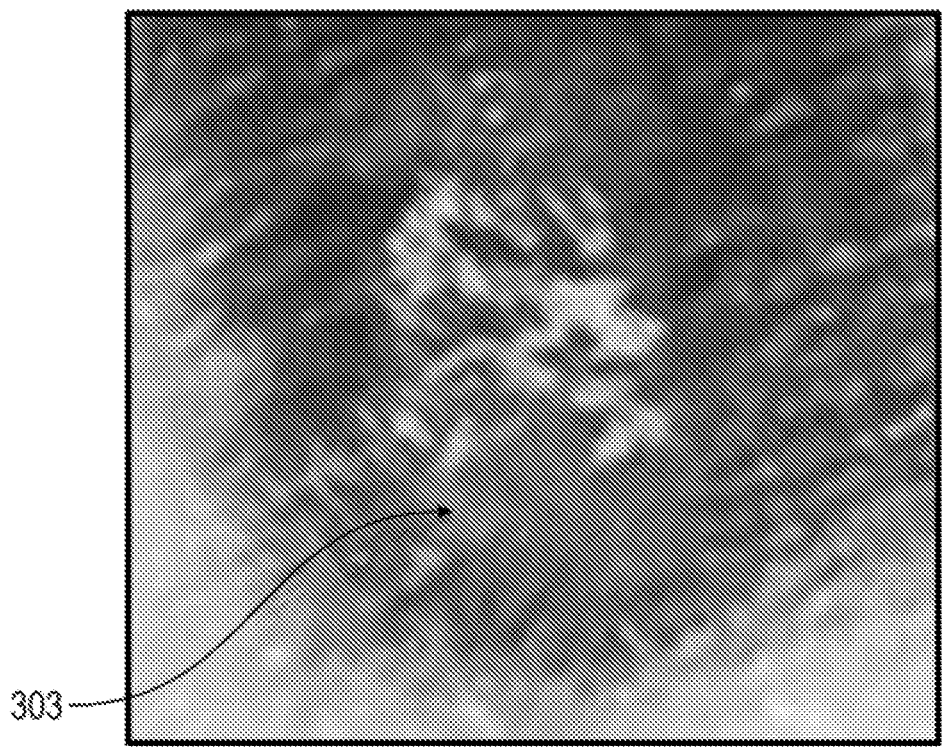

FIGS. 3A-3C illustrates one example of a tattoo treatment in which electrical energy was applied to assist in removal of pigmentation (dye) from a tattoo. In this example, skin 300 was treated with pulsed electrical energy applied as 200 ns long pulses at 30 kV/cm using a 2.5×2.5 mm electrode at 6 Hz. 100 pulses, total were delivered. FIG. 3A shows the example of the tattoo region of the skin shortly after treatment showing the treatment region 303. Following three months post-treatment, much of the tattoo pigment was absent from the treated area (region) 303, as shown in FIG. 3B and in the enlarged view of FIG. 3C. In this example, electrical energy was applied without the addition of any adjunctive therapy to further break up the tattoo ink. As will be described in greater detail below, the use of an adjunctive therapy to further break apart the ink (rather than just the macrophages) may result in further ink clearance.

Figure 3D:
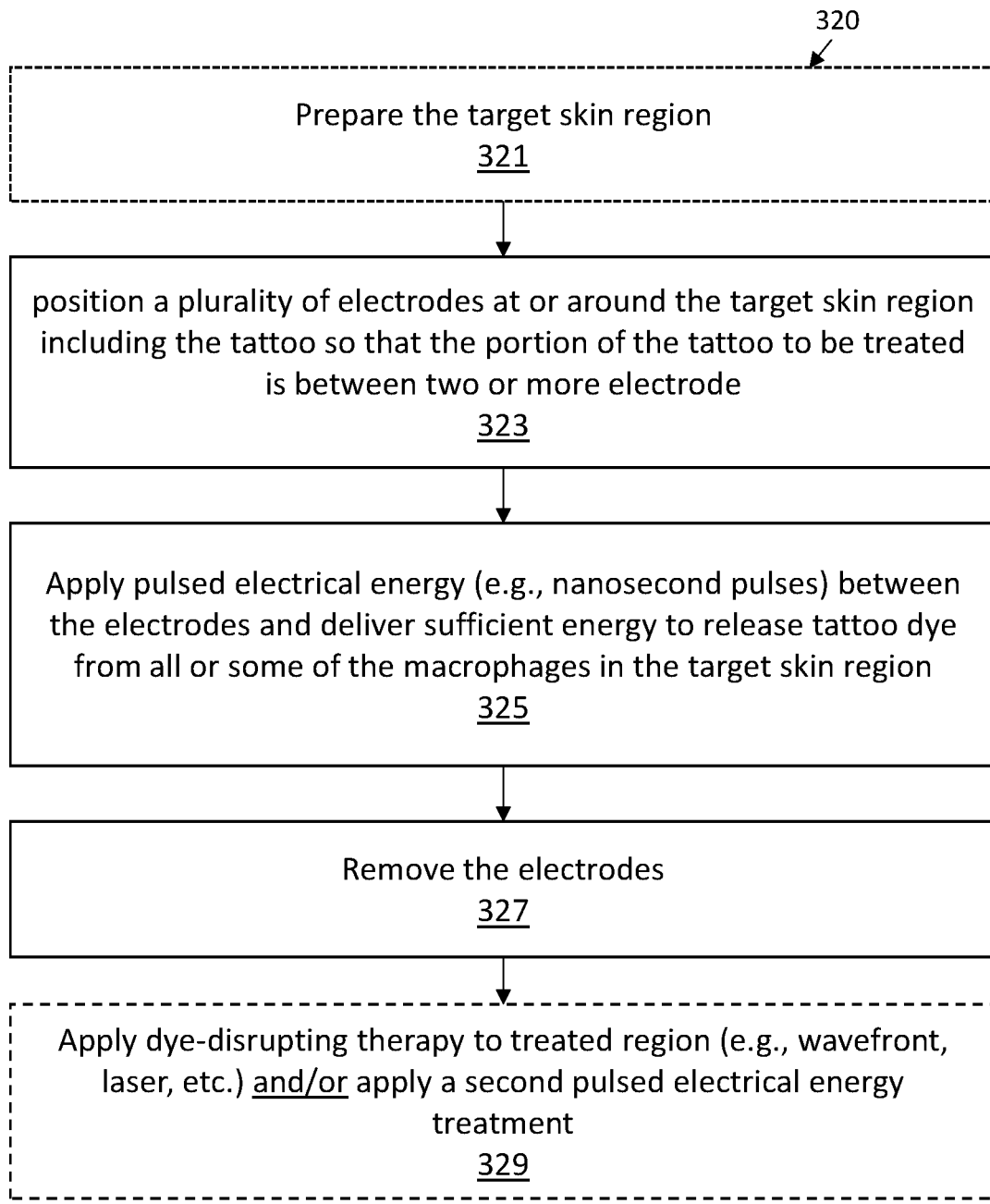
FIG. 3D illustrates one example of a method of treating tissue to remove a tattoo, as described herein.

FIG. 3D illustrate one example of a method 320 of treating a tattoo. A method such as the method shown schematically in FIG. 3D may be used to release tattoo pigmentation (e.g., by disrupting dermal macrophages that have encapsulated the pigmentation). This method may be (or may be part of) a method of removing or reducing a tattoo. For example, in FIG. 3D, the region of the tissue to be treated may be first prepared 321. This region is the region of skin including the tattoo. In general, the region may be prepared by cleaning it. The skin may be shaved or otherwise prepared. A conductive or electrically insulating cover (e.g., an insulating gel) may be applied over the region to be treated; the applicator tip, including the electrodes, may be inserted through the conductive gel. An applicator tip, e.g., including a plurality of electrodes may be positioned around the first treatment region to be treated. In some variations described herein, tissue penetrating needles electrodes may be inserted into the skin to the target depth (e.g., 1-3 mm deep) 323. Once positioned, pulsed electrical energy, including in particular nanosecond pulsed electrical energy, may be applied between the electrodes to disrupt (in some variations destroying) some or all of the macrophages in the target region 325. This step may be repeated by moving the electrodes over or skin including the tattoo until the entire region has been treated. The energy applied may be sufficient to release some or all of the tattoo ink (e.g., dye) from the macrophages containing the tattoo ink. The applicator tip (e.g., electrodes) may then be removed 327.

In any of the methods, additional treatments, such as a second, or more, pulsed electrical energy (e.g., pulsed electrical energy having a pulse duration in sub-microsecond pulse range) treatments may be applied 329. The second treatment may be performed after a delay period of, e.g., between 2 hours and 14 days (e.g., between 12 hours and 14 days, 12 hours or more, 24 hours or more, 5 days or more, 7 days or more, etc.). The parameters used for the second treatment of pulsed electrical energy having a pulse duration in sub-microsecond pulse range may be the same or different. In some variations more energy may be applied for the first treatment than the second treatment. In some variations, less energy may be applied for the second treatment. The first and second treatment regions may be the same or overlapping (e.g., the second treatment region may encompass the first treatment region. In some variations a larger second treatment region may be treated, enclosing the first treatment region and adjacent skin, which may have been separately treated.

In any of these methods, as described in greater detail below, one or more accessory treatments for breaking apart the larger ink particles may be used. These accessory treatments may be integrated into any of the methods and apparatuses described herein. For example, in FIG. 3D, the method may include applying one or more dye-disrupting therapies (e.g., accessory therapies) to the treated region(s). The accessory therapy may be applied concurrent the application of the electrical energy. In some variations the dye-disrupting therapy may be applied after the application of electrical energy but before new macrophages have arrived into the treatment region. This may be, for example, before 3 months, before 2.5 months, before 2 months, before 1.5 months, before 1 months, etc., from the application of the electrical energy described above. For example, the accessory therapy may be between 1 minute and 3 months after the application of pulsed electrical energy to the target (tattooed) region. In some variation the skin may be allowed to recover for 1-7 days before the application of the accessory therapy. In some variations the skin may be treated within a few minutes of the electrical therapy (e.g., between 1 min and 24 hours).

Figure 10A:
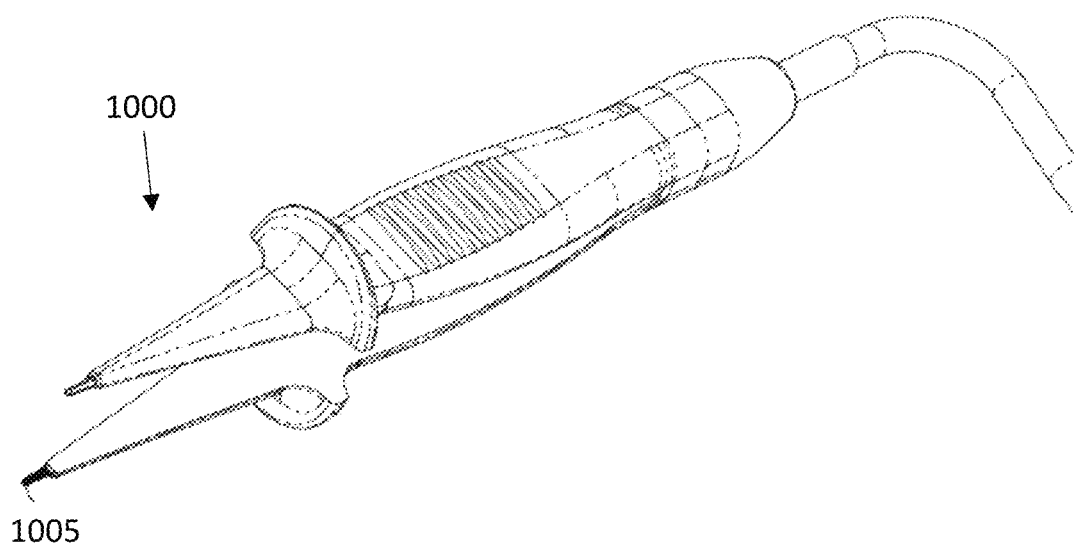
FIG. 10A illustrates one example of an applicator configured as a pair of electrodes arranged in a forceps configuration, with one or more electrodes one each of two arms arranged so that tissue (e.g., a target region of skin) may be held between the arms to deliver a pulsed electrical energy as described herein.
Figure 10B:
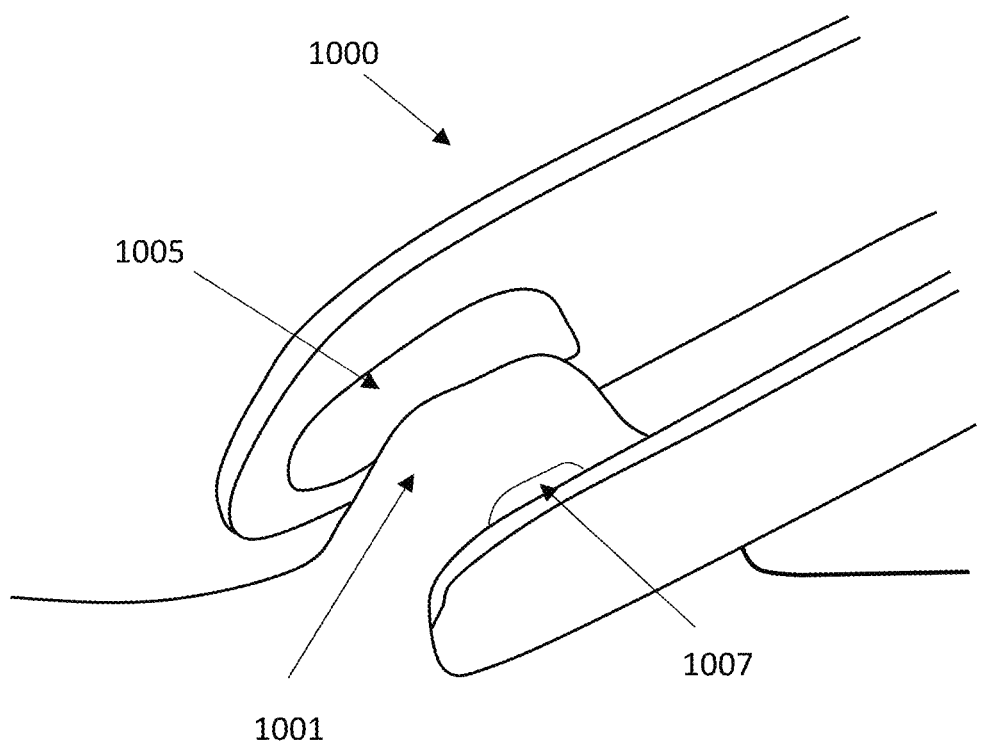
FIG. 10B illustrates one example of an applicator configured as a forceps including a plurality of electrodes that may be used to apply energy to a region of tissue.

In some variations, non-penetrating electrodes may be used. For example, the tip shown in FIG. 4D illustrates one example of a treatment tip having non-penetrating electrodes. In some variations, the target skin region may be held or positioned so that they are between the electrodes without penetrating the skin (or in addition to penetrating the skin). For example, the electrodes may be part of a pair of grasping jaws (e.g., a forceps-like structure, which may be formed as a forceps-like electrode), as illustrated in FIGS. 10A and 10B. As shown in FIG. 10A, the applicator, which may be configured as an applicator tip, is configured as forceps 1000 and includes a pair of arms that each include one or more electrodes 1005 on the distal tip region. As shown in FIG. 10B, the electrodes may be configured as surface electrodes such that the tissue 1001 (e.g., skin tissue) including a tattoo may be pinched and held between the two or more surface electrodes 1005. The jaws of the applicator may be opened and the target tissue (e.g., a region including a tattoo) may be held between the jaws and therefore the electrodes, pushing the electrodes into the skin (but not penetrating the skin).

It will be apparent that the number of steps of the methods that are utilized are not limited to those described above. Also, the methods do not require that all the described steps are present. Although the methodology described above as discrete steps, one or more steps may be added, combined or even deleted, without departing from the intended functionality of the embodiments of the disclosure. The steps can be performed in a different order or have the steps shared between more than one processor, for example. It will also be apparent that the method described above may be performed in a partially or substantially automated fashion, including performed using robotic systems.

An apparatus for treating skin to remove a tattoo may include a pulse generator, a set of electrodes, and a controller configured to control, at least partially, operation of the pulse generator. The controller may comprise a processor having a set of instructions, wherein the set of instructions, when executed by the processor causes the pulse generator to generate and apply through the set of electrodes a pulsed electrical treatment to a region of tissue to disrupt macrophages within the target tissue region (e.g., by de-nucleation) without provoking a substantial inflammatory response. Any of the apparatuses described herein may include, for example, a hand-held applicator having a hand piece. For example, FIG. 4A shows an example of a hand piece 401 that may plug (via cord 403) to a generator (not shown) for generating the pulsed electrical energy. One or more different tips may couple with the hand piece; the tips may include the electrode(s) for delivering the energy to the skin, as described above. For example, FIGS. 4B-4D, and FIGS. 6A-8B, illustrate exemplary electrode tips for treating skin by delivering pulsed electrical energy as described herein. In FIG. 4A, the tip 405 fits over the distal end of the hand piece 401, and snaps or locks in place once electrical contact is made with the projecting (needle-like) electrodes 411. For example, the tip may be mechanically secured (e.g., by snap-fit, friction fit, etc.) onto the end of the hand piece. In FIG. 4B, two electrodes are provided, and each is sufficiently sharp so that it may penetrate the skin. One electrode may be the cathode and the other electrode the anode. The electrodes may be pointed and/or sharp, or otherwise configured to penetrate the tissue. FIG. 4C shows a tip 407 that includes two parallel rows of sharp, tissue penetrating electrodes that may all simultaneously penetrate the skin in the region including or surrounding the target skin region. Alternatively, only some of the electrodes may penetrate the skin. In this example, the electrodes (or electrode pairs) may be separately addressed by the apparatus, or they may be connected together. For example, in FIG. 4C, the left row of electrodes may be electrically connected (e.g., acting as a cathode) and the right row of electrodes may be electrically connected (e.g., acting as an anode).

In any of the penetrating electrodes described herein, the needles may be configured to penetrate the tissue only to the region of the skin including the ink (e.g., the dermal macrophages that have encapsulated the ink). This is typically between about 1 mm and 2 mm, which is a standard depth for most tattoo needles. In some variations slightly shallower and/or slightly deeper (e.g., between 0.5-3 mm, etc.) may be used. Limiting the depth may further assist in targeting the macrophages as described herein.

FIG. 4D illustrates an example of a non-penetrative (e.g., surface) tip 409 including electrodes that are configured to deliver, for example, pulsed electrical energy as described herein. In FIG. 4D, an outer ring of electrode surrounds an inner electrode; these electrodes may act as an electrode pair for delivering energy (e.g., current) to the skin. The tips in FIGS. 4B-4D may be swapped. While not shown, instead of being hand-held, an applicator may be configured for attachment to a movable arm of the robotic system. The movement and/or operation of such applicator may be computer-controlled.

FIG. 5 illustrates an example of an applicator tip including needle electrodes that are configured to deliver electrical energy, as described herein. In this example, a plurality of outer electrodes (e.g., ground electrodes) surround an inner electrode (e.g., delivery electrode).

Figure 6A:
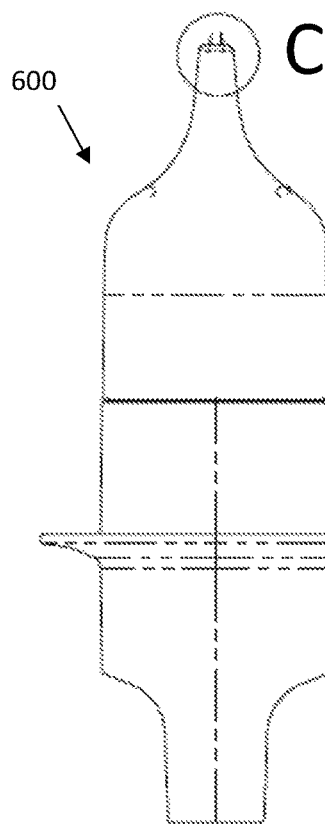
FIGS. 6A-6F illustrate an example of an applicator tip with a plurality of needle electrodes, showing an array of six electrodes forming a 1.5 mm×1.5 mm box.
Figure 6B:
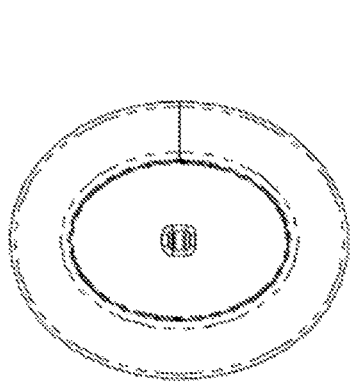
Figure 6C:
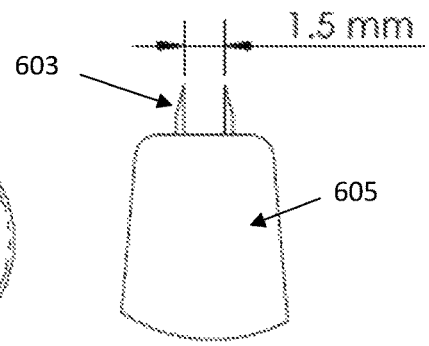
Figure 6D:
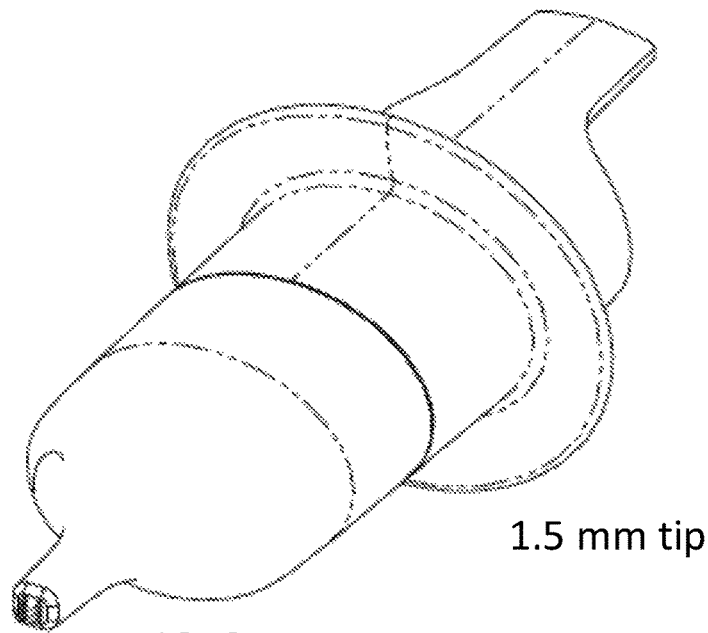
Figure 6E:
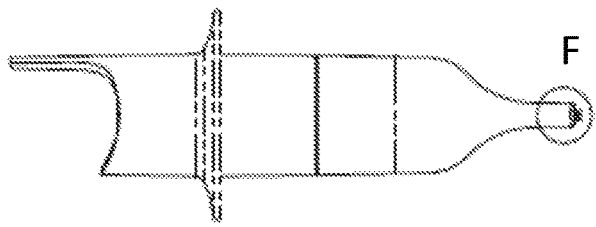
Figure 6F:
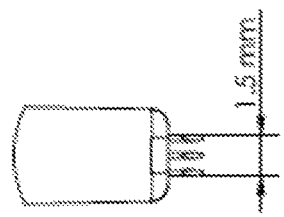
Figure 7A:
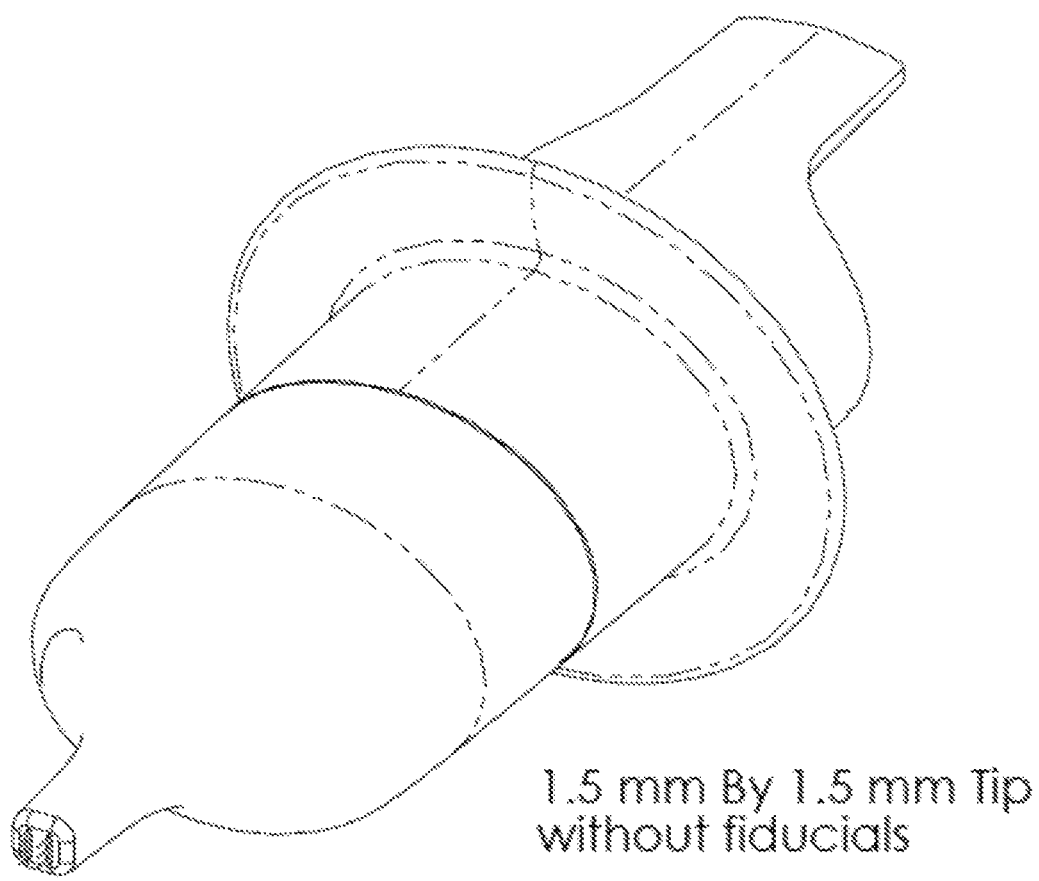
FIGS. 7A-7B illustrate another example of an applicator tip with an array of electrodes (e.g., needle electrodes). The two lines of electrodes (extending 1.5 mm) are spaced 1.5 mm apart.
Figure 7B:
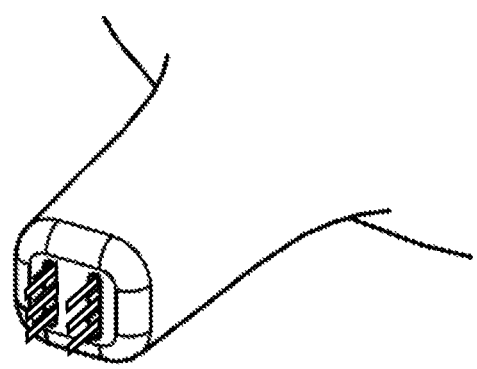

FIGS. 6A-6F show different views of one example of a treatment tip. In this example the treatment tip is shown that may be attached to the hand piece or other component for connection to the controller and generator. FIGS. 6C and 6F show enlarged views of the distal end of the tip 600, including the six electrodes 603 extending from an insulated base 605. Similarly, FIGS. 7A-7B show perspective views of a 1.5 mm×1.5 mm, including an enlarged view of the electrode extending (2 mm) from the base of the electrode tip region. While some applicator tips may comprise fiducials, the example of the applicator tip of FIG. 7A does not have fiducials.

Figure 8A:
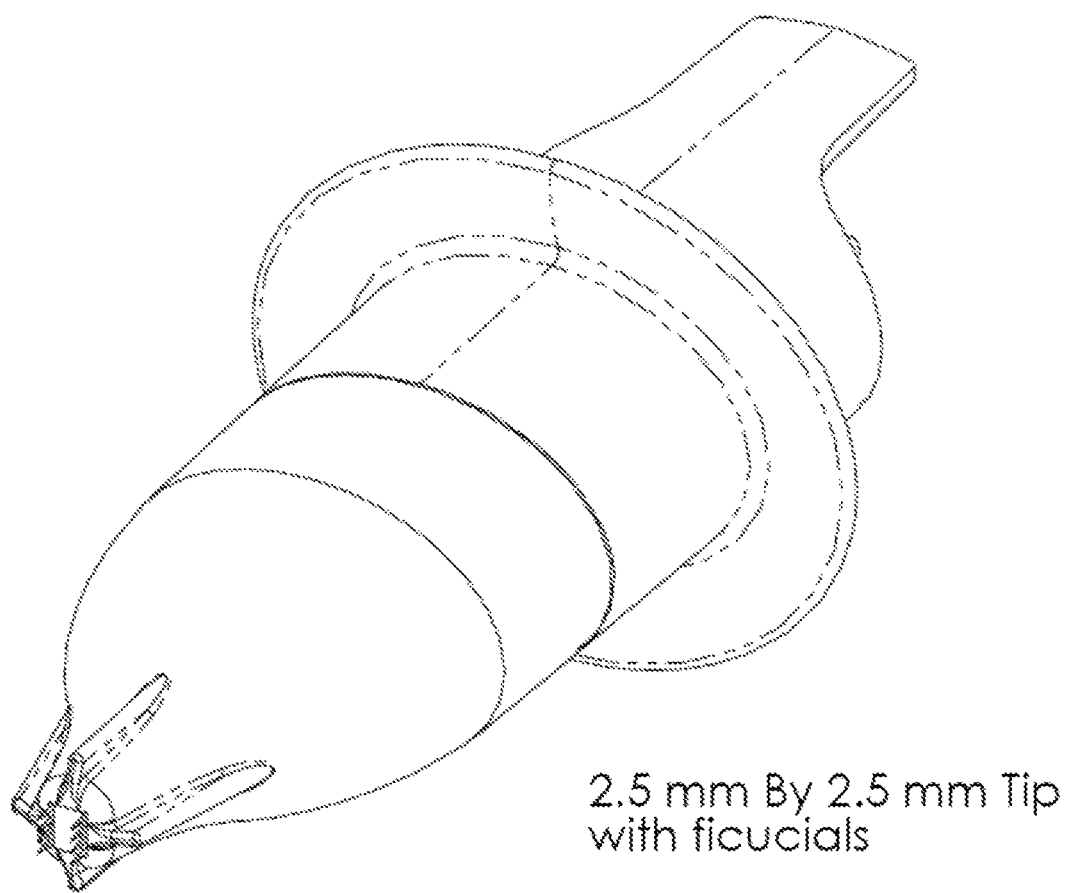
FIGS. 8A-8B illustrate another example of an applicator tip with an array of electrodes (e.g., needle electrodes). The two lines of electrodes (extending 2.5 mm) are spaced 2.5 mm apart.
Figure 8B:
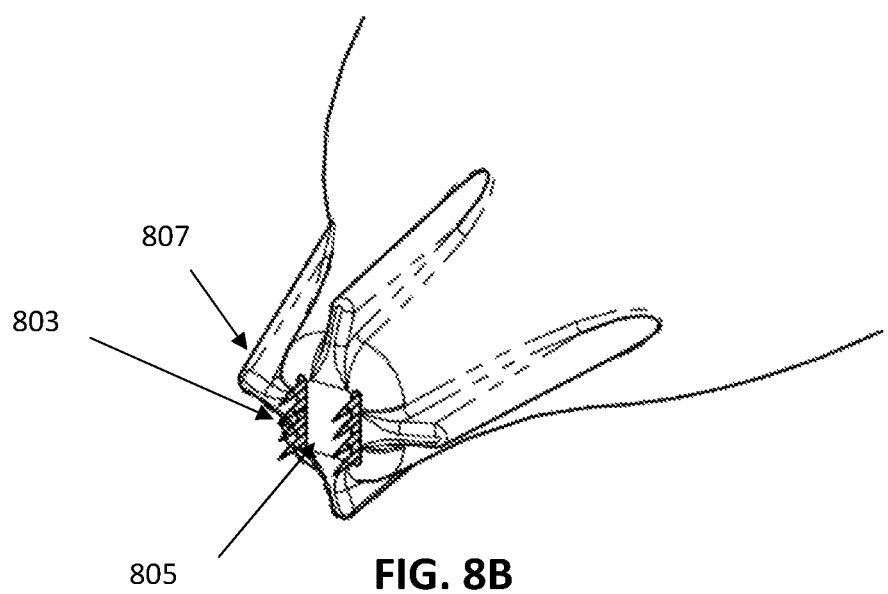

FIGS. 8A and 8B shows an alternative view of a tip of an applicator that includes eight electrodes 803 extending from the base 805. In this example the applicator tip also includes fiducial marking regions 807 that form a "+" shape with the electrodes in the central region. The fiducial alignment region may be used to align the treatment tip with the target region of the skin.

Figure 9A:
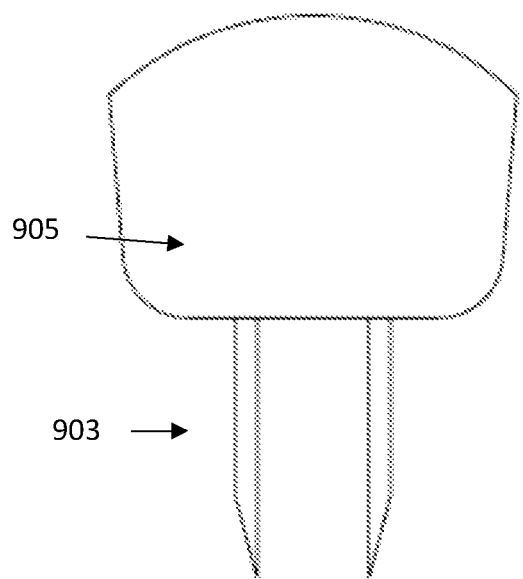
FIGS. 9A-9D illustrate examples of electrodes (shown as needle electrodes).
Figure 9B:
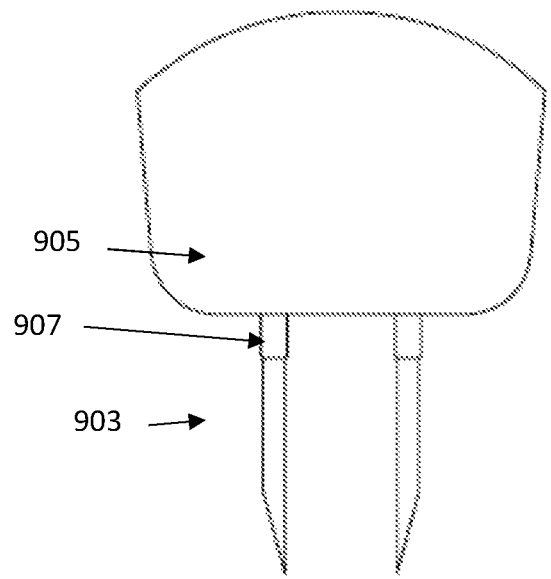
Figure 9C:
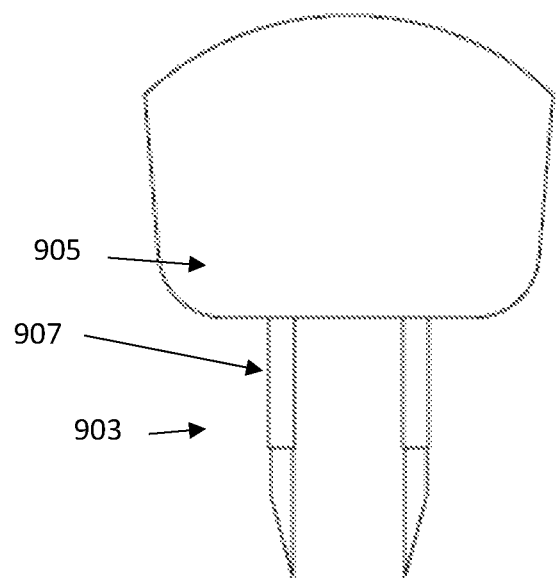
Figure 9D:
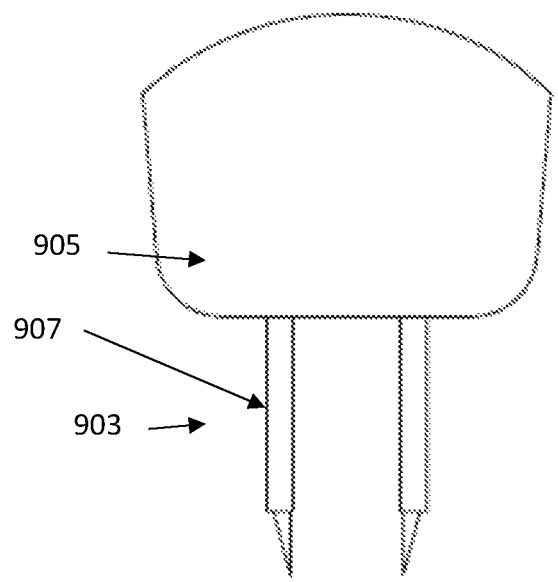

In any of the variations described herein, the treatment tip may include insulated (or partially insulated electrodes). Specifically, the tissue-penetrating electrodes may be insulated over the region near the base of the electrode to limit the energy applied at this region, which will correspond to the more surface region of the tissue when the electrode have been inserted into the skin. Typically, the dermal macrophages including ink may be located between 1-2 mm deep into the skin; thus it may be desirable to target this depth of the tissue specifically; this targeting may be achieved by electrically insulating the portion of the tissue-penetrating electrodes that extend above and/or below this depth. For example, FIG. 9A shows an example of a pair of electrodes 903 extending from a base 905. The base may be electrically insulated. The electrodes may extend, for example, 1-2 mm or more. Any portion of these electrodes may be insulated, as shown in FIGS. 9B-9D. The extent of the insulation 907 on the electrodes may be selected to protect the dermis and/or epidermis, and particularly to protect the adnexal structures near the skin and other structures adjacent to the target region. Since the target region may be at about 1 mm-2 mm deep, the region between the base 905 and about 1 mm may be insulated, as shown in FIGS. 9B and 9C. Alternatively, the majority of the electrodes 903 may be insulated (e.g., 907), as shown in FIG. 9D.

In some variations, the electrodes applying the energy may be rotated partway through the application of the treatment. In some implementations, automated, including computer controlled, systems may provide precise and accurate rotating and repositioning of the energy delivery device (e.g., rotation of the electrode pattern) in the same treatment region or zone. Rotation, as used here, may refer to the rotation of the pattern of two or more electrodes, including (but not limited to) tissue penetrating electrodes, such as needle electrodes. Rotation of the pattern of electrodes may be relative to a target tissue region. In general, the rotated pattern may be rotated by any amount of rotation (e.g., between 0.5 degrees to 359.5 degrees, such as between 5 degrees and 355 degrees, between 10 degrees and 350 degrees, between 20 degrees and 340 degrees, between 30 degrees and 330 degrees, between 40 degrees and 320 degrees, approximately 90 degrees, etc.). The rotation may be clockwise and/or counterclockwise. Rotation may be physical rotation of the pattern of electrodes (e.g., the applicator) relative to the tissue, or rotation by changing the active electrodes of an array of electrodes so that the pattern of active electrodes is rotated relative to the target tissue. The pattern of electrodes may be rotated relative to a region of tissue (e.g., a target region of tissue) so that after rotation the treatment is applied to the same region of tissue. For example, the treatment tip may be positioned on the same region of the tissue before and after rotation. Any of the apparatuses described herein may be implemented in robotic systems that may be used to position and/or control the electrodes during a treatment. For example, a system may include a robotic arm to which is coupled an applicator, such as an energy delivery device, having an applicator tip with a plurality of electrodes. Various motors and other movement devices may be incorporated to enable fine movements of an operating tip of the applicator in multiple directions. The robotic system may further include at least one image acquisition device (and preferably two for stereo vision, or more) which may be mounted in a fixed position or coupled (directly or indirectly) to a robotic arm or other controllable motion device. The operating tip of the applicator may be positioned over a tissue region to be treated.

Accessory Therapies

As mentioned above, any of the methods and apparatuses described herein for treatment of a tattoo may include the use of a non-electrical therapy targeting the affected skin region, such as one or more of: kinetic energy (e.g., vibrational/sonic energy), thermal treatment (e.g., cryotherapy), phototherapy (e.g., the use of light, including laser energy), in addition to the use of the high-field strength, short electrical pulses of energy.

For example, an acoustic shockwave may be used to generate force sufficient to disrupt large cluster of dye following destruction or disruption of the macrophages within the tattooed skin. The shockwave may be an ultrasound shockwave that is tuned to target the dye within the tissue in the same region of the tissue as the treatment region. Example of shockwave-generated device may include rapid pulse electrohydraulic shockwave generating devices that, for example generate acoustic shockwaves at a rate of between 10 Hz and 5 MHz. The acoustic shockwave may be at an energy and/or frequency that does not substantially target the cells or tissue, but may break apart the dye. Thus, in conjunction with the application of high-field strength, short electrical pulses of energy to disrupt and/or destroy the macrophages, may result in the rapid clearance of the dye by new macrophages over the days following the treatment.

The use of lasers to treat tattoos is well known, including the use of Q-switched and picosecond lasers to target dyes. Typically the energy applied by the laser is sufficient to both break apart the dye, and must also be sufficient to disrupt or destroy the macrophages surrounding the dye. Unfortunately, this may result in scarring and/or altering of natural pigmentation. Further, such techniques are not usually fully effective, which may be due in part to the failure to disrupt the macrophages. Thus, it may be particularly beneficial to include laser light treatment in conjunction with the macrophage-targeting electrical therapies described herein. For example, a laser having a frequency targeting one or more tattoo dye color may be applied at a relatively low energy (e.g., typically lower by X % than used for tattoo removal, where X is 10%, 15%, 20%, 25%, 30%, 35%, 40%, 45%, 50%, 60%, 70%, 80%, 90%, etc.). The laser energy may be applied after or during the electrical disruption of the macrophages as described above.

EXAMPLES

The use of pulsed electrical energy having a pulse duration in sub-microsecond pulse range to remove a tattoo was examined in an animal model. Preliminary data from a human patient (see, e.g., FIGS. 11A-11D) indicated that the application of pulsed electrical energy having a pulse duration in sub-microsecond pulse range may release ink from macrophages, as described above. For example, FIG. 11A, shows a region of skin including a tattoo immediately after it has been treated by the application of 3.2 J of energy applied with a 2.5×2.5 applicator tip (resulting in an energy density of about 256 J/cc). The applicator tip included an array of needle electrodes that penetrated the skin as shown. FIG. 11B shows the same region of skin one day after the procedure. Five days after the procedure (FIG. 11C), the skin showed healing, and over the next few months a gradual reduction in ink from the treated region was observed. By 90 days after the treatment (FIG. 11D), the tattoo ink had substantially cleared from the treated region.

To examine this effect, animals (mice) were tattooed, and the resulting tattooed skin was treated by the application of pulsed electrical energy having a pulse duration in sub-microsecond pulse range using various treatment parameters including the amount of energy applied and/or the number of treatments.

Figure 12A:
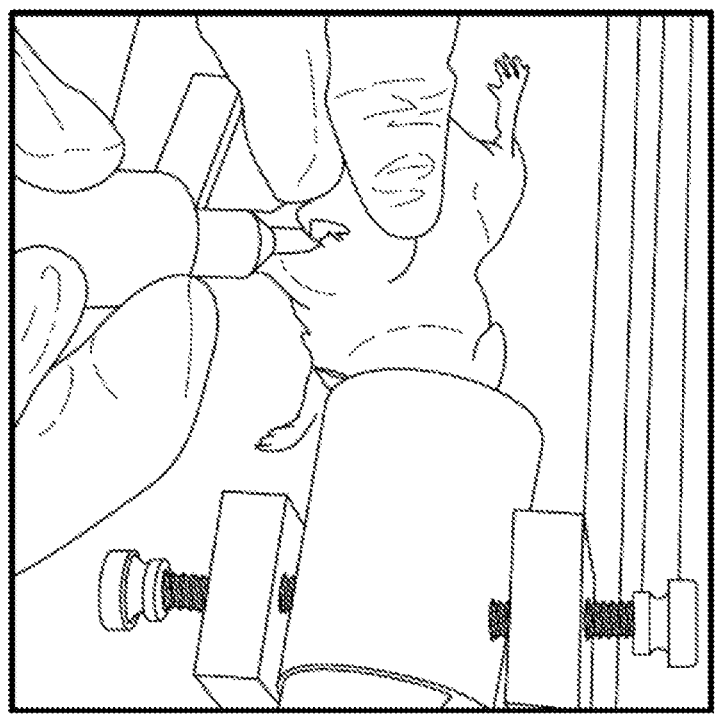
FIGS. 12A and 12B illustrate the application of tattoos on test animals (mice) treated as described herein.
Figure 12B:

FIGS. 12A and 12B illustrate the animal models used. Mice were tattooed with an "X" shape (as shown in FIG. 12A) on both sides, to define regions for treatment. Tattoo formation was examined. After tattooing, mice were allowed to recover for 3-4 weeks, to allow for macrophage engulfment of dye particles. As expected, melanophages within each mouse took up the tattoo ink and remained resident in the tattooed dermis indefinitely. This is illustrated in FIGS. 13A-13F. Skin samples were biopsied at 3, 10 and 25 days after tattoos were applied to the mouse skin. Histological analysis indicates that melanophages take up the ink within 10 days and tattoos were stabilized within 25 days. By 25 days following the tattoo application the tattoo ink was encapsulated in macrophages. FIGS. 13A and 13D show micrographs of a region of mouse skin three days after tattooing. FIGS. 13B and 13E illustrate another tattooed region of skin 10 days after tattooing. FIGS. 13C and 13F show another region of tattooed skin 25 days after tattooing.

Tattooed mice were treated with pulsed electrical energy having a pulse duration in sub-microsecond pulse range using various different settings. A 2.5×2.5 mm treatment tip (having an array of needle electrodes) was used. The skin was examined to identify and characterize the effects.

As shown in FIGS. 14A-14D, treating tattoos with pulsed electrical energy having a pulse duration in sub-microsecond pulse range generally released the tattoo ink from the melanophages.

Figures 14A, 14B, 14C, 14D:
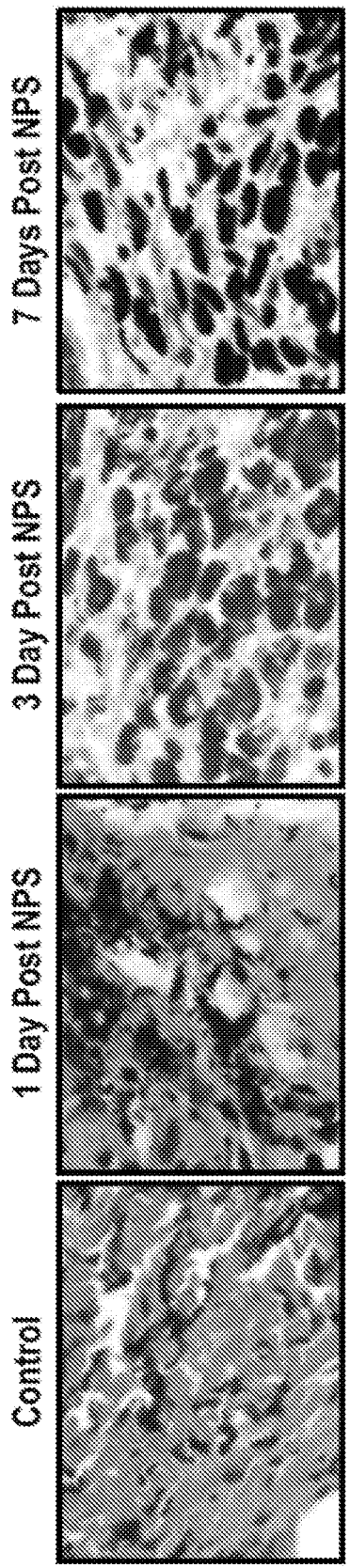
FIG. 14A-14D show magnified images of the sections through control (FIG. 14A) and treated tattooed skin one day after treatment (FIG. 14B), three days after treatment (FIG. 14C) and 7 days after treatment (FIG. 14D) with high-field strength, short electrical pulses.

FIG. 14A shows a control region of tattooed skin prior to the application of pulsed electrical energy having a pulse duration in sub-microsecond pulse range. Ink particles are visible in clusters, at least partially encapsulated, resulting in discrete ink regions. Following one day post-treatment with pulsed electrical energy having a pulse duration in sub-microsecond pulse range (FIG. 14B), the ink particles are shown released into less well-defined regions. In some cases, following treatment, some or all of the ink particles may simply be taken back up by melanophages (e.g., within 7 days following treatment). FIGS. 14B-14D show high magnification images of mouse skin tattoos at indicated times after treatment with pulsed electrical energy having a pulse duration in sub-microsecond pulse range. Dye leaks out following NPS treatment for at least 3 days (FIGS. 14B and 14C). But by day 7 the dye has been encapsulated by macrophages (e.g., melanophages).

Various treatment regimens were examined, including low energy (e.g., 1.5, 3 and 4.5 J) treatments, moderate energy (e.g., 4.5 J, 6 J and 7.5 J) treatments, single treatments and multiple treatments.

The application of pulsed electrical energy having a pulse duration in sub-microsecond pulse range was generally found to release tattoo ink from regions of tattooed skin. This may be due, in part, to the pulsed electrical energy having a pulse duration in sub-microsecond pulse range targeting and non-thermally breaking down pigment laden macrophages and fibroblasts in the upper and mid-dermis. In some cases, released ink was cleared via the lymphatic system. In general, these treatments were "color blind" and thus may work for all ink colors. In some cases, the pulsed electrical energy having a pulse duration in sub-microsecond pulse range also affects cells in the dermis so could clear ink in minimal number of treatments. Although one treatment may be successfully used, in some cases it may be advantageous to use multiple treatments (e.g., two or more treatments at some interval of time apparat, such as, e.g., great than: 6 hours, 12 hours, 24 hours, 36 hours, 48 hours, 3 days, 4 days, 5 days, 6 days, 7 days, etc. between treatments). In some cases, at least two treatments separated by about 24 hours worked to release ink; in some cases, two treatments separated by 7 days apart worked well to eliminate ink from the tattooed skin. Treating two times between about 1 day and 10 days (e.g., between about 1-7 days, greater than 1 day, greater than 2 days, etc.) apart appears to clear ink from tattooed skin using fairly low energy (e.g., between about 1.5-4.5 J). A second treatment may result in the ink moving up to the epidermis to be trapped in the crust that forms during the period following the treatment.

Figure 15:
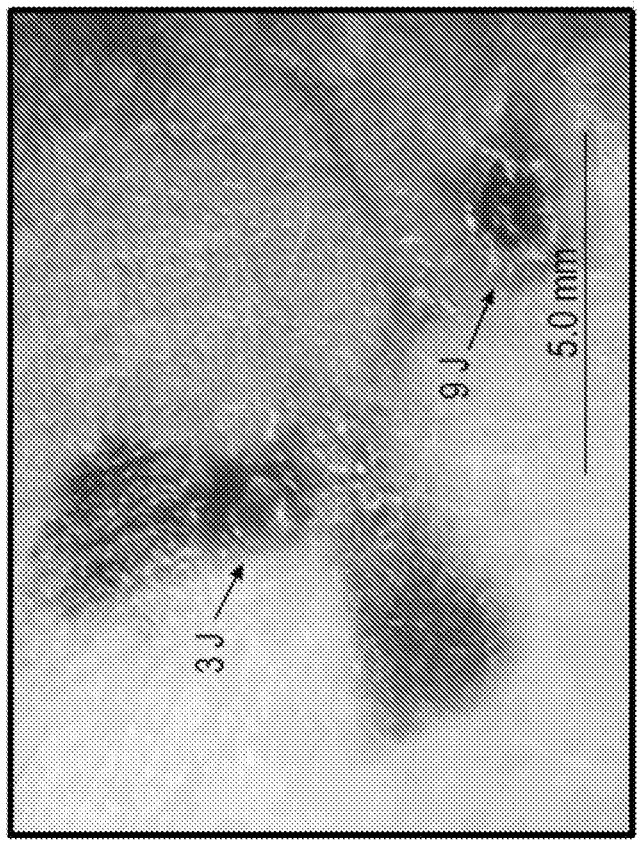
FIG. 15 shows an image of a region of tattooed skin treated in two regions with different energy levels of high-field strength, short electrical pulses (e.g., 3 J and 9 J).

FIG. 15 is an image showing a tattooed region of a mouse in which two different regions of the tattoo are treated with different energies (3 J and 9 J). FIGS. 16A-F show enlarged views of the treated (FIGS. 16A and 16B) and control/untreated (FIG. 16C) images of the surface of the skin, and below the surface sections through the treated skin regions taken ten days after treatment with high-field strength, short electrical pulses (delivering 3 J in FIG. 16D and 9 J in FIG. 16E) or untreated (FIG. 16F). For example, FIGS. 16A and 16D show the surface of the skin region of tattooed skin and corresponding histological section below the surface 10 days after the 3 J treatment; FIGS. 16B and 16E show the surface of the skin region of tattooed skin and corresponding histological section below the surface 10 days after 9 J treatment; and FIGS. 16C and 16F show an untreated control region of the surface of the skin and the corresponding histological section below the surface.

Figure 17A:
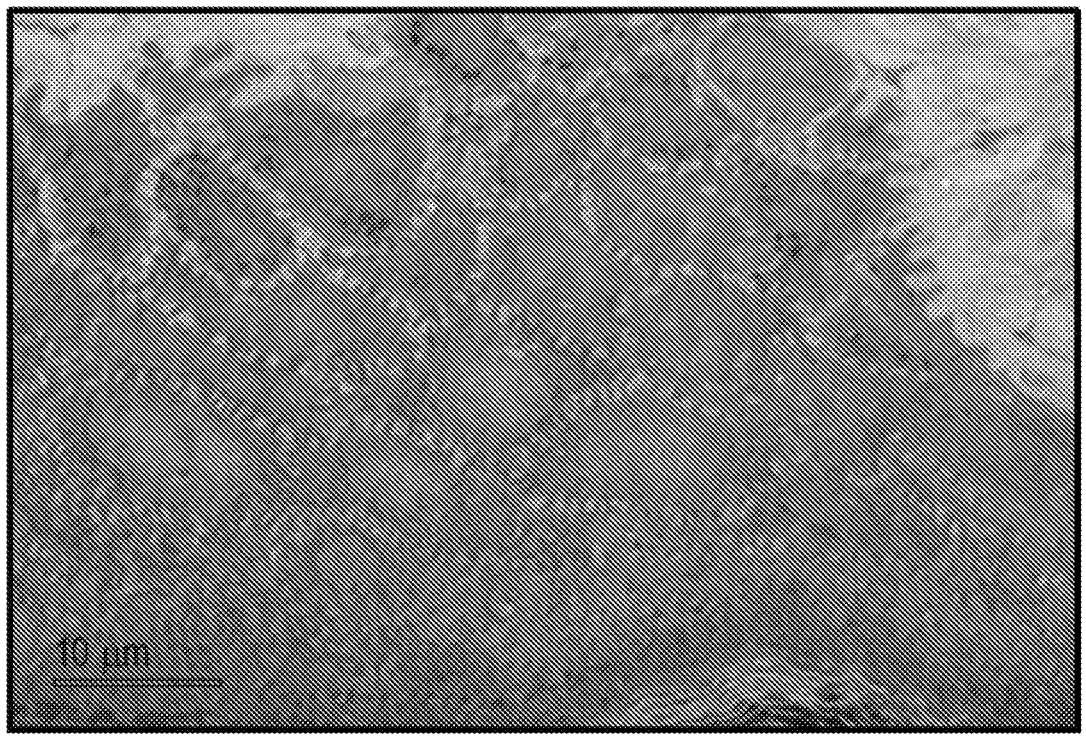
FIGS. 17A and 17B are electron micrographs through tattooed skin before treatment (FIG. 17A) and seven days after treatment with high-field strength, short electrical pulses.
Figure 17B:
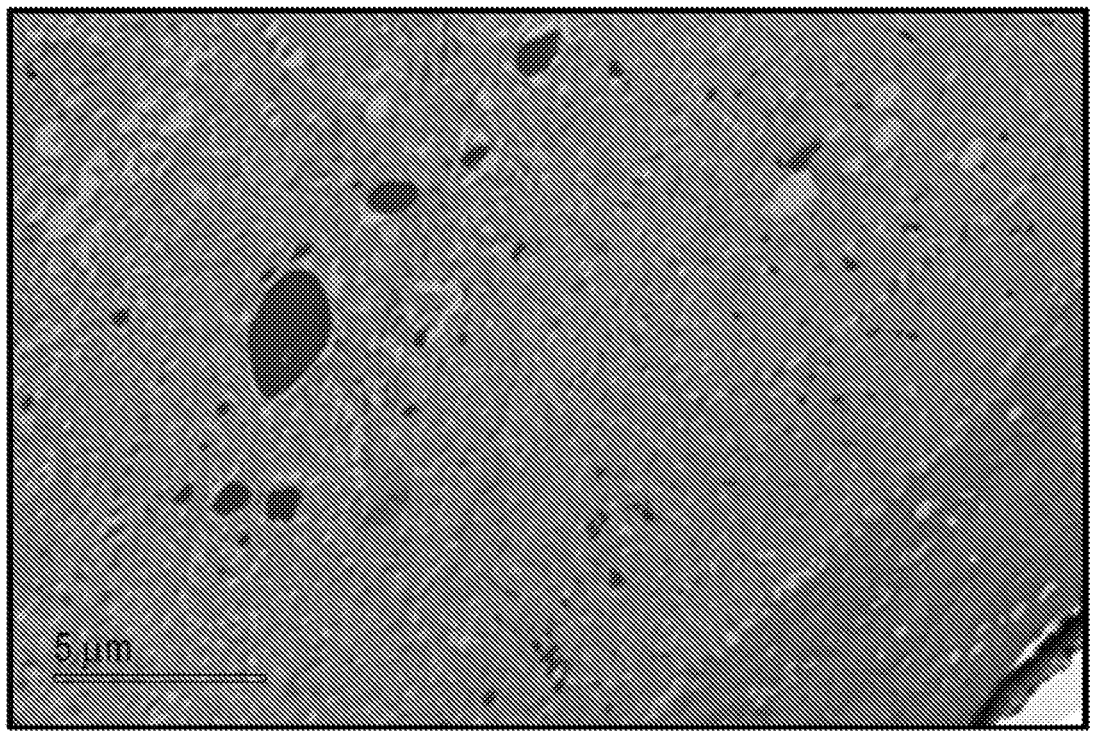
Figure 18A:
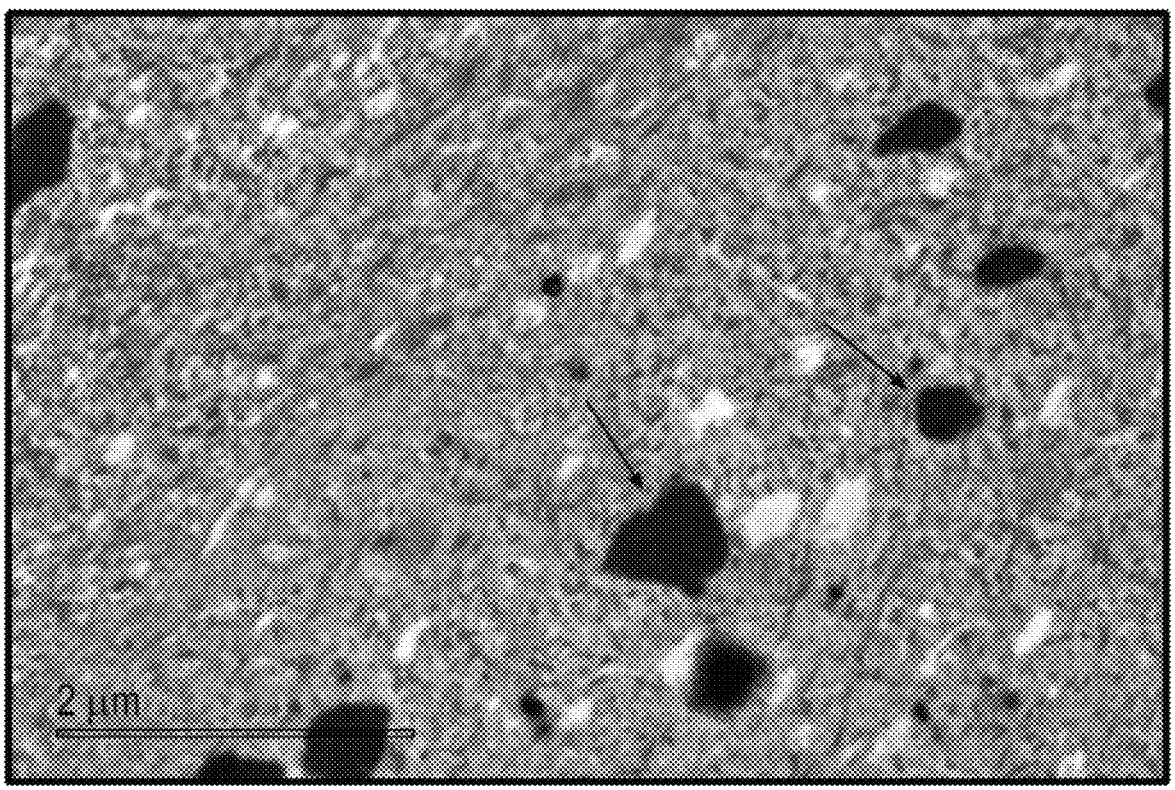
FIGS. 18A and 18B are electron micrographs of tattooed skin treated with high-field strength, short electrical pulses, showing regions of skin that were treated seven days after treatment.
Figure 18B:
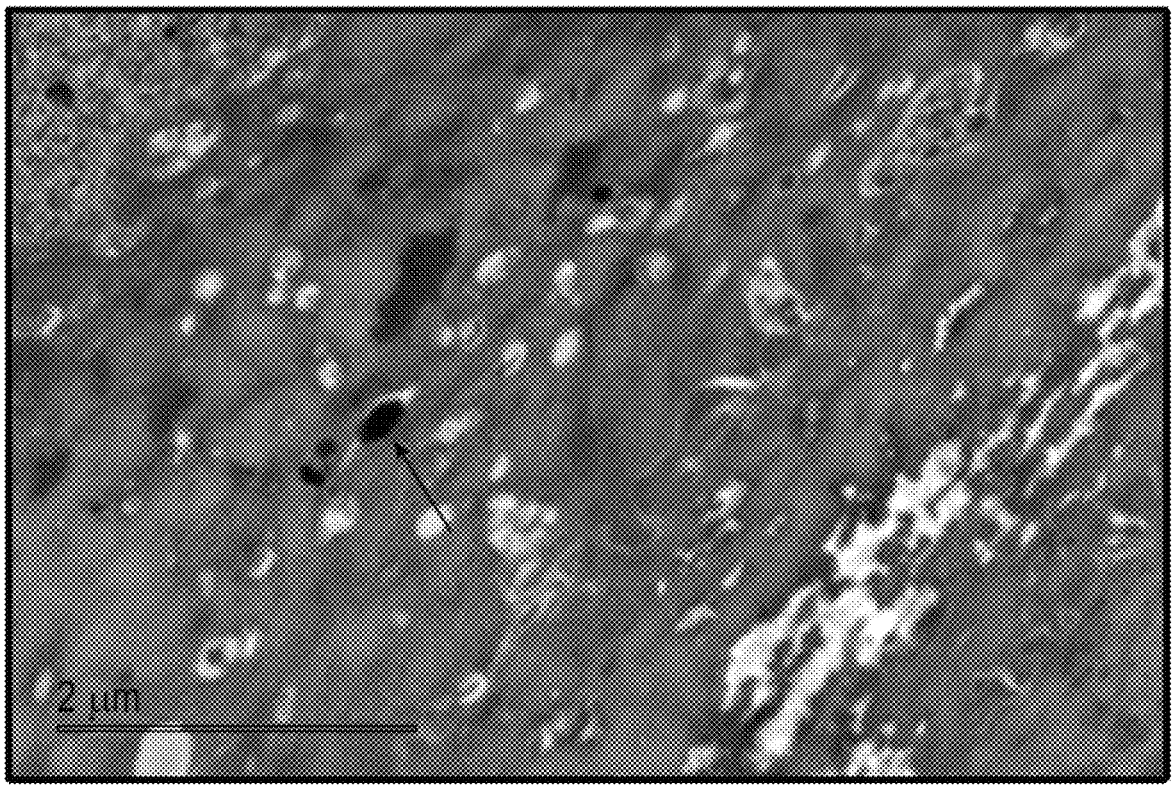
Figure 19A:
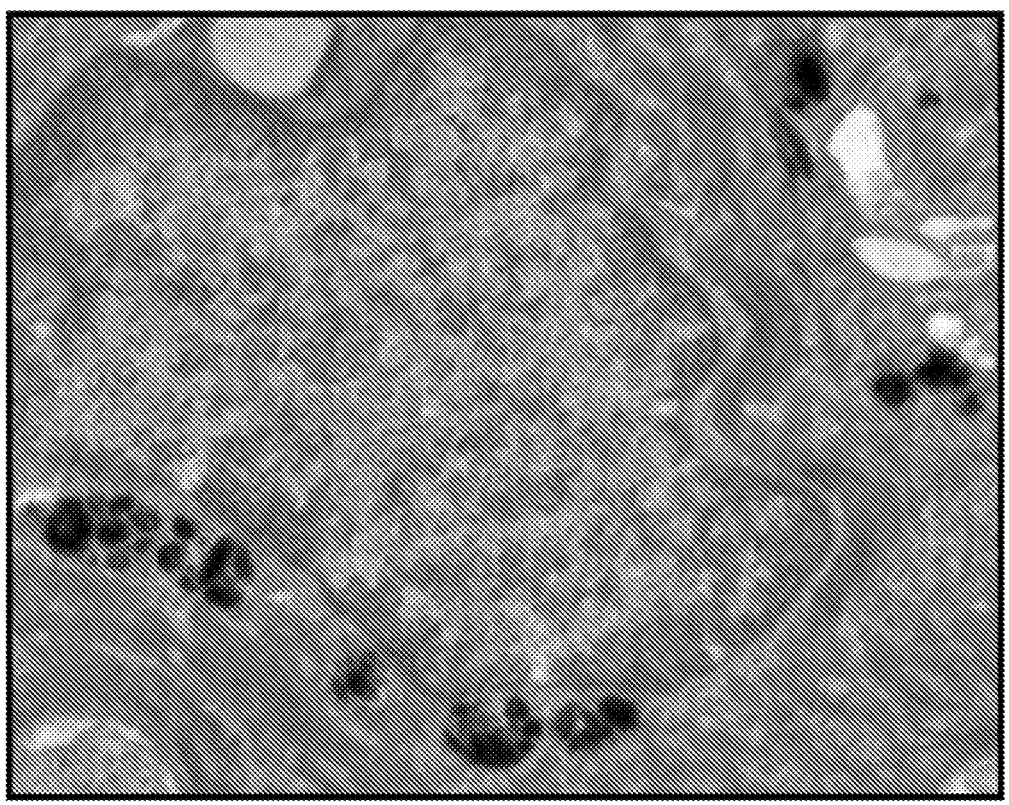
FIG. 19A is an electron micrograph of a region of untreated (control) tattooed skin.
Figure 19B:
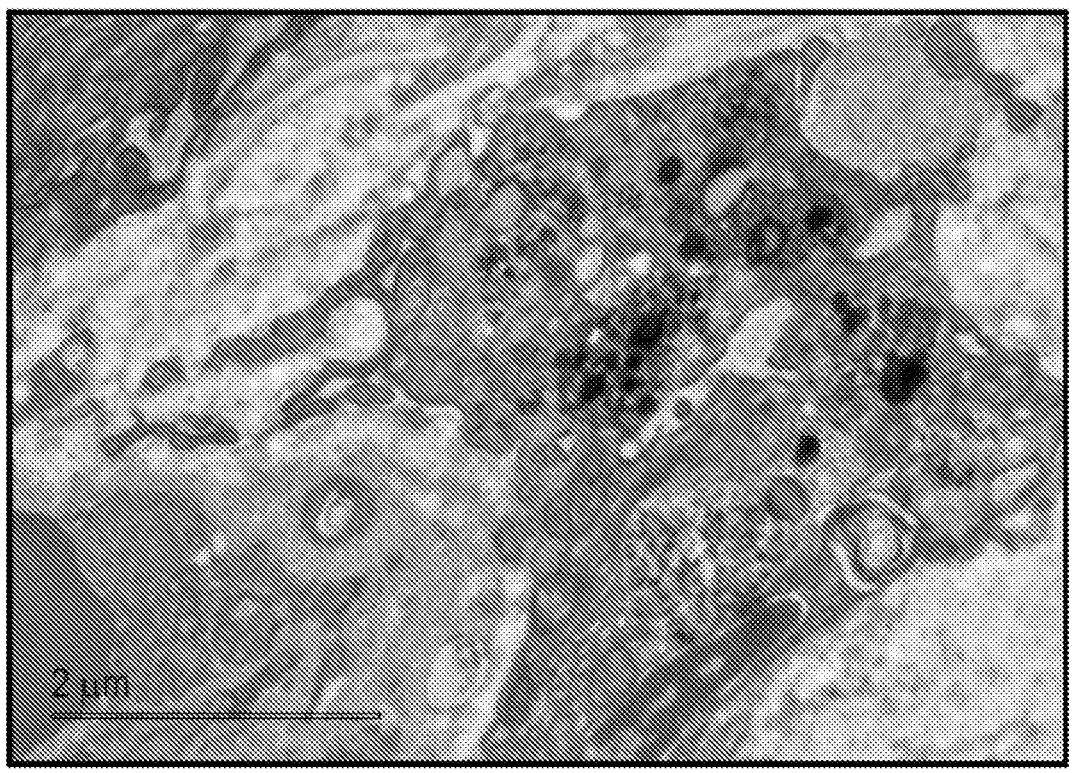
FIG. 19B shows a comparable tattooed region of skin seven days after treatment with high-field strength, short electrical pulses.
Figure 20A:
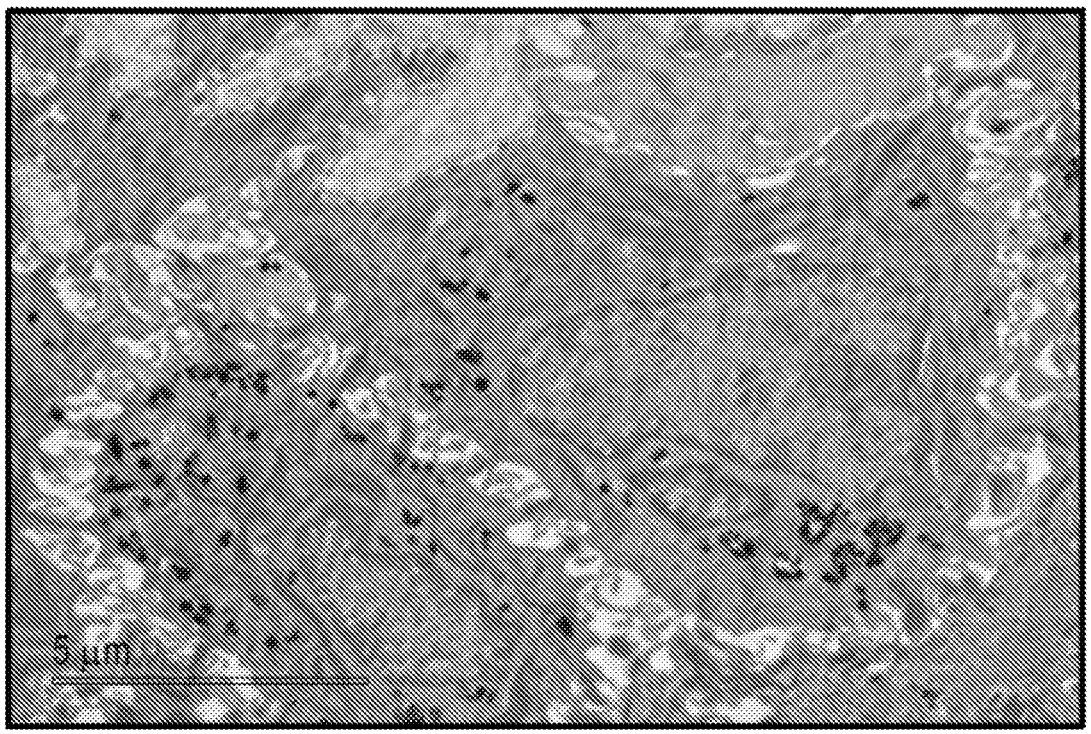
FIGS. 20A and 20B are electron micrographs of tattooed regions of skin before treatment (FIG. 20A) and 14 days after treatment with high-field strength, short electrical pulses (FIG. 20B). Both images are at 1500× magnification.
Figure 20B:
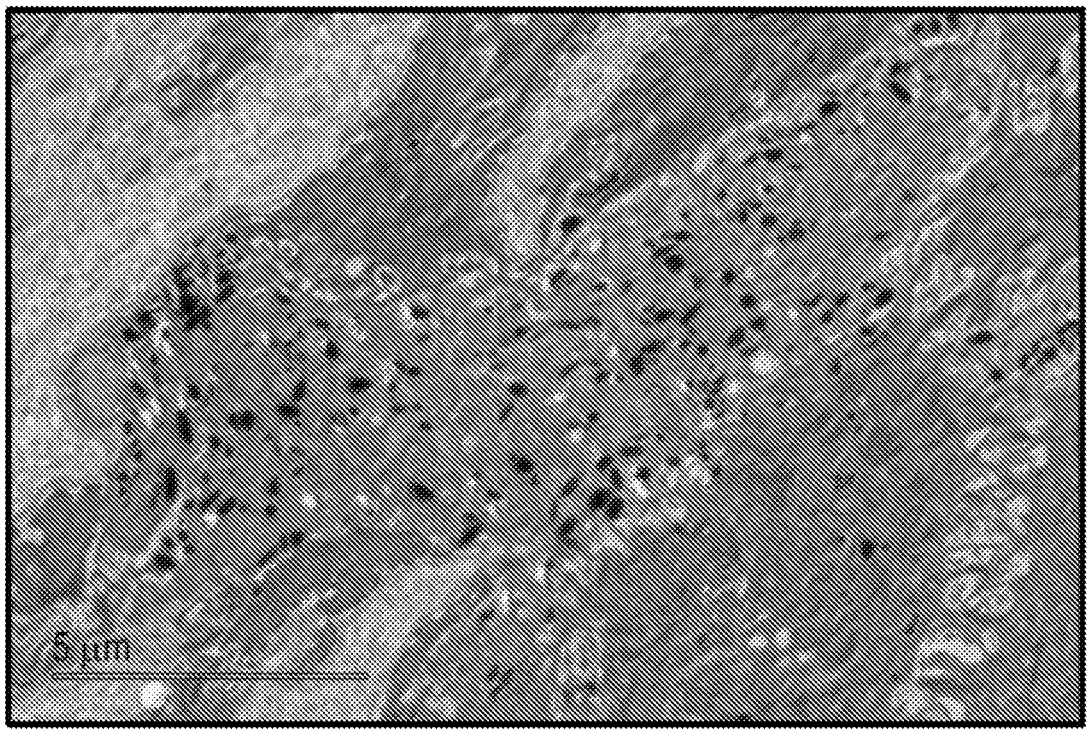

FIGS. 17A and 17B are electron micrographs of tattooed mouse skin before (FIG. 17A, at 400×) and seven days after treatment by the application of pulsed electrical energy having a pulse duration in sub-microsecond pulse range (FIG. 17B, at 1000×). Similarly, FIGS. 18A and 18B show electron micrographs of treated tattooed mouse skin seven days following a treatment with pulsed electrical energy having a pulse duration in sub-microsecond pulse range, at 4000×. These images show amorphous pigment (ink, arrows) in damaged cells and stratum corneum. FIGS. 19A-19B show enlarged views of a control region (FIG. 19A) and a region 7 days after treatment (FIG. 19B). In FIG. 20A, a tattooed region of skin before treatment is shown (1500×); FIG. 20B shows a tattooed region of skin following treatment (1500×).

As mentioned above, in some variations, multiple treatments with pulsed electrical energy having a pulse duration in sub-microsecond pulse range may be used, separated by a time interval (e.g., between 12 hours and 10 days, such as, e.g., 7 days or more). FIGS. 21A-21D show a time course for four different treated tattooed skin regions each treated with a first pulsed electrical energy having a pulse duration in sub-microsecond pulse range, at three different power levels (e.g., 1.5 J, 3 J and 4.5 J) and then treated with the same power level a second time after waiting 24 hours. For example, FIGS. 21A1, 21B1, 21C1 and 21D1 show tattooed skin regions for four different mice prior to treatment with pulsed electrical energy having a pulse duration in sub-microsecond pulse range. For each of these images, three regions of tattooed skin were identified and treated with the different power level, as indicated by the labeled arrows in each figure. After 24 hours the same regions were treated with the same level of treatment, and the mice were allowed to recover. Images were then captured for the same regions at day 7 following the initial treatment (FIGS. 21A2, 21B2, 21C2, and 21D2), at 10 days from the initial treatment (FIGS. 21A3, 21B3, 21C3 and 21D3), at 12 days from the initial treatment (FIGS. 21A4, 21B4, 21C4 and 21D4), at 14 days from the initial treatment (FIGS. 21A5, 21B5, 21O5 and 21D5), and at 17 days from the initial treatment (FIGS. 21A6, 21B6, 21O6 and 21D6).

Histological sections of tattooed skin fixed at various times after treatment show that no dye remained in the skin for all tattoos treated twice, as shown in FIGS. 22A1-22A4, 22B1-22B4, 22C1-22C4, 22D1-22D4, 22E1-22E4 and 22F1-22F4) at various times post-treatment (1 day, 3 days, 7 days, or 14 days, respectively. In contrast, untreated skin (e.g., control tattooed skin), showed no change in ink in the tissue, as shown in FIGS. 22A5, 22B5, 22C5, 22D5, 22E5, 22F5, respectively.

FIGS. 23A1-23D6 show a similar array of images taken from tattooed mice that were treated with a single, higher energy treatment (e.g., 4.5 J, 6 J or 7.5 J). In the absence of any supplemental treatment (including laser or other dye-removing treatment), in some cases the tattoo dye may remain and may again be engulfed and retained by macrophages. FIG. 23A1 show images prior to treatment, and FIGS. 23A2-23A6 show a time course following a single treatment with pulsed electrical energy having a pulse duration in sub-microsecond pulse range treating three different regions of the tattoo with 4.5 J, 6 J or 7.5 J, as shown. Similar images are taken for three other treated mice (FIGS. 23B1-23B6, FIGS. 23C1-23C6, FIGS. 23D1-23D6).

As mentioned above, tattooed skin may be repeatedly treated with pulsed electrical energy having a pulse duration in sub-microsecond pulse range, which may enhance clearance of tattoo dye from the treated regions. Repeating treatments in the way may be effective even when lower powered treatments (e.g., less than 3 J) are used. The duration of time between treatments may be generally between 12 hours and 14 days or more, such as in some variations 7 days or more. For example, FIGS. 24A1-24H6 show the effects of treatment over seven different mice. FIGS. 24A1-24A6 each show three treated regions (treated with 1.5 J, 3 J, and 1.5 J) at day 0 and again at day 7 with pulsed electrical energy having a pulse duration in sub-microsecond pulse range (the same treatment parameters/power was applied in each region between day 0 and day 7). FIG. 24A1 shows the tattooed skin to be treated prior to the treatment (day 0), while FIGS. 24A2-24A6 show the same tattooed skin region at day 7 (prior to the second treatment), day 10, day 12, day 14 and day 17, respectively. Similar results are shown for seven other mice, e.g., 24B1-24B6, 24C1-24C6, 24D1-24D6, 24E1-24E6, 24F1-24F6, 24G1-24G6 and 24H1-24H6.

Embodiments of the methods of the present disclosure may be implemented using computer software, firmware or hardware. Various programming languages and operating systems may be used to implement the present disclosure. The program that runs the method and system may include a separate program code including a set of instructions for performing a desired operation or may include a plurality of modules that perform such sub-operations of an operation or may be part of a single module of a larger program providing the operation. The modular construction facilitates adding, deleting, updating and/or amending the modules therein and/or features within the modules.

In some embodiments, a user may select a particular method or embodiment of this application, and the processor will run a program or algorithm associated with the selected method. In certain embodiments, various types of position sensors may be used. For example, in certain embodiment, a non-optical encoder may be used where a voltage level or polarity may be adjusted as a function of encoder signal feedback to achieve a desired angle, speed, or force.

Certain embodiments may relate to a machine-readable medium (e.g., computer readable media) or computer program products that include program instructions and/or data (including data structures) for performing various computer-implemented operations. A machine-readable medium may be used to store software and data which causes the system to perform methods of the present disclosure. The above-mentioned machine-readable medium may include any suitable medium capable of storing and transmitting information in a form accessible by processing device, for example, a computer. Some examples of the machine-readable medium include, but not limited to, magnetic disc storage such as hard disks, floppy disks, magnetic tapes. It may also include a flash memory device, optical storage, random access memory, etc. The data and program instructions may also be embodied on a carrier wave or other transport medium. Examples of program instructions include both machine code, such as produced by a compiler, and files containing higher level code that may be executed using an interpreter.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to perform or control performing of any of the steps, including but not limited to: displaying, communicating with the user, analyzing, modifying parameters (including timing, frequency, intensity, etc.), determining, alerting, or the like. In some exemplary embodiments hardware may be used in combination with software instructions to implement the present disclosure.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting. For example, as used herein, the singular forms "a", "an" and "the" are intended to include the plural forms as well, unless the context clearly indicates otherwise. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present apparatuses and methods.

The terms "comprises" and/or "comprising," when used in this specification (including the claims), specify the presence of stated features, steps, operations, elements, and/or components, but do not preclude the presence or addition of one or more other features, steps, operations, elements, components, and/or groups thereof. Unless the context requires otherwise, "comprise", and variations such as "comprises" and "comprising," means various components can be co-jointly employed in the methods and articles (e.g., compositions and apparatuses including device and methods).

Any of the apparatuses and methods described herein may include all or a sub-set of the components and/or steps, and these components or steps may be either non-exclusive (e.g., may include additional components and/or steps) or in some variations may be exclusive, and therefore may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the disclosure as described by the claims. For example, the order in which various described method steps are performed may often be changed in alternative embodiments, and in other alternative embodiments one or more method steps may be skipped altogether. Optional features of various device and system embodiments may be included in some embodiments and not in others.

Therefore, the foregoing description is provided primarily for exemplary purposes and should not be interpreted to limit the scope of the apparatuses and methods as it is set forth in the claims.

Various embodiments may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A system comprising:
    a pulse generator;
    an applicator having a plurality of electrodes, the applicator configured to apply energy from the pulse generator to the plurality of electrodes; and
    a controller configured to control, at least partially, operation of the pulse generator, the controller comprising a processor having a set of instructions which, when executed by the processor, causes the application of a pulsed electrical energy having a pulse duration in a sub-microsecond pulse range through the plurality of electrodes to a target region of a skin comprising a tattoo such that the pulsed electrical energy is delivered at a density between about 0.01 J/mm$^3$ and about 1.5 J/mm$^3$ to cause a release of a tattoo ink from macrophages within the target region of the skin.

2. The system of claim 1, wherein the same or a different controller is configured to control, as least partially, the operation of the applicator.

3. The system of claim 1, wherein the applicator comprises a set of electrodes and the plurality of electrodes is a subset of the set of electrodes.

4. The system of claim 1, further comprising one or more dye-disrupting therapy applicators, the one or more dye-disrupting therapy applicators configured to apply a dye-disrupting therapy to the target region of skin to break up clusters of dye.

5. The system of claim 4, wherein the one or more dye-disrupting therapy applicators comprises at least one of the following: a sonic transducer, a thermal transducer, and/or a laser-light transducer.

6. The system of claim 4, wherein the controller is configured to coordinate the application of the dye-disrupting therapy from the one or more dye-disrupting therapy applicators and the application of the pulsed electrical energy.

7. The system of claim 6, wherein the controller is configured to apply the dye-disrupting therapy concurrently with the application of the pulsed electrical energy.

8. The system of claim 1, wherein the applicator is configured to allow the plurality of electrodes to be inserted between up to 3 mm deep into the target region of the skin.

9. The system of claim 1, wherein the controller is configured to deliver the pulsed electrical energy at an energy density of between about 0.03 J/mm$^3$ and about 0.09 J/mm$^3$.

10. The system of claim 1, wherein the pulsed electrical energy has a pulse duration between 0.01 nanoseconds and 1000 nanoseconds.

11. The system of claim 1, wherein each electrode of the plurality of electrodes comprises a needle electrode extending or extendable proud of a base of the applicator, further wherein each needle electrode includes an insulated base portion and uninsulated tip portion.

12. The system of claim 11, wherein the insulated base portion extends between at least 0.1 and 1 mm from the base of the applicator.

13. The system of claim 11, wherein the uninsulated tip portion extends between 1 and 3 mm from the base of the applicator.

14. The system of claim 1, wherein the controller is configured to cause the application of the pulsed electrical energy having a peak field strength of at least 0.1 kV/cm.

15. The system of claim 1, wherein the controller is configured to cause the application of the pulsed electrical energy for less than 5 minutes or for less than 1000 pulses.

16. A system comprising:
    a movable arm;
    an applicator having a plurality of electrodes, wherein the applicator is operatively coupled to the movable arm and configured to apply pulsed electrical energy from the plurality of electrodes; and
    one or more processors comprising a set of instructions for executing operations, the set of instructions including instructions for:

moving the movable arm to contact a target region of tissue comprising a tattoo with the applicator;

directing application of the pulsed electrical energy to the target region of tissue, wherein the pulsed electrical energy has a pulse duration in a sub-microsecond pulse range and electrical energy at a density between about 0.01 J/mm$^3$ and about 1.5 J/mm$^3$ to cause a release of a tattoo ink from macrophages within the target region of the skin.

17. The system of claim 16, further comprising a navigation interface comprising an image acquisition device.

18. The system of claim 17, wherein the navigation interface is configured to receive imaging data and determine a path for treatment based on the pigmentation of the target region of the skin.

19. The system of claim 17, wherein the navigation interface is configured to determine a distance between the target region and the plurality of electrodes to allow control and guidance of the applicator relative to the target region.

20. The system of claim 17, wherein the navigation interface is configured to determine an orientation of the plurality of electrodes relative to the target region to allow control and guidance of the treatment tip relative to the target tissue.

21. The system of claim 16, further comprising one or more dye-disrupting therapy applicators configured to apply a dye-disrupting therapy to the target region of skin to break up clusters of dye.

22. The system of claim 16, wherein the one or more dye-disrupting therapy applicators comprises one or more of: a sonic transducer, a thermal transducer, and/or a laser-light transducer.

23. The system of claim 22, wherein the one or more processors is configured to coordinate application of a dye-disrupting therapy from the one or more dye-disrupting therapy applicators and the application of the pulsed electrical energy.

24. The system of claim 16, wherein the set of instructions further comprises instructions to control insertion of the plurality of electrodes between 1 mm and 3 mm deep into the target region of the skin.

25. A machine-readable tangible medium storing instructions for causing one or more machines to execute operations for:

applying a plurality of electrodes on or into a subject's skin so that a target region of skin including a tattoo is between two or more of the plurality of electrodes; and applying pulsed electrical energy having a pulse duration in a sub-microsecond pulse range between the two or more of the plurality of electrodes, wherein the pulsed electrical energy is delivered at a density between about 0.01 J/mm$^3$ and about 1.5 J/mm$^3$ to release a tattoo ink from macrophages within the target region of skin.

* * * * *